(12) United States Patent
Flohr et al.

(10) Patent No.: US 7,166,587 B2
(45) Date of Patent: Jan. 23, 2007

(54) CARBAMIC ACID ALKYL ESTER DERIVATIVES

(75) Inventors: Alexander Flohr, Basel (CH); Guido Galley, Rheinfelden (DE); Roland Jakob-Roetne, Inzlingen (DE); Eric Argirios Kitas, Aesch (CH); Jens-Uwe Peters, Grenzach-Wyhlen (DE); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 187 days.

(21) Appl. No.: 10/951,229

(22) Filed: Sep. 27, 2004

(65) Prior Publication Data

US 2005/0075327 A1    Apr. 7, 2005

(30) Foreign Application Priority Data

Oct. 6, 2003   (EP) ................... 03022650

(51) Int. Cl.
C07D 243/18 (2006.01)
C07D 243/12 (2006.01)
A61K 31/55 (2006.01)
A61K 31/5513 (2006.01)
A61P 25/28 (2006.01)

(52) U.S. Cl. ............... 514/212.04; 514/221; 540/517; 540/522

(58) Field of Classification Search ............ 540/517, 540/522; 514/212.04, 221
See application file for complete search history.

(56) References Cited

FOREIGN PATENT DOCUMENTS

| WO | WO 00/38618 A2 | 7/2000 |
| WO | WO 01/77086 A1 | 10/2001 |
| WO | WO 01/92235 A1 | 12/2001 |
| WO | WO 04/069826 A1 | 8/2004 |

OTHER PUBLICATIONS

Sisodia, S. et al., Nature Reviews/Neuroscience vol. 3, Apr. 2002 pp. 281-290.
Beher, D. et al., Biochemical Society Transactions (2002), vol. 30, Part 4, pp. 534-537.
Wolfe, M. S., Current Topics in Medicinal Chemistry, (2002), vol. 2, pp. 371-383.
Tsai, J. Y. et al., Current Medicinal Chemistry (2002) vol. 9, No. 11, pp. 1087-1106.
Sambamurti, K. et al., Drug Development Research vol. 56 (2002), pp. 211-227.
May, P. C., Drug Discovery Today, vol. 6, No. 9 (2001) pp. 459-462.
Nunan, J. et al., FEBS Letters vol. 483 (2000) pp. 6-10.
Hardy, J. et al., Science, vol. 297 (2002) pp. 353-356.
Wolfe, M. S., Journal of Medicinal Chemistry vol. 44, No. 13 (2001) pp. 2039-2060.

*Primary Examiner*—Bruck Kifle
(74) *Attorney, Agent, or Firm*—George W. Johnston; Patricia S. Rocha-Tramaloni; Kimberly J. Prior

(57) ABSTRACT

The present invention provides compounds of the general formula

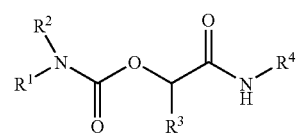

I wherein
$R^4$ is one of the following groups

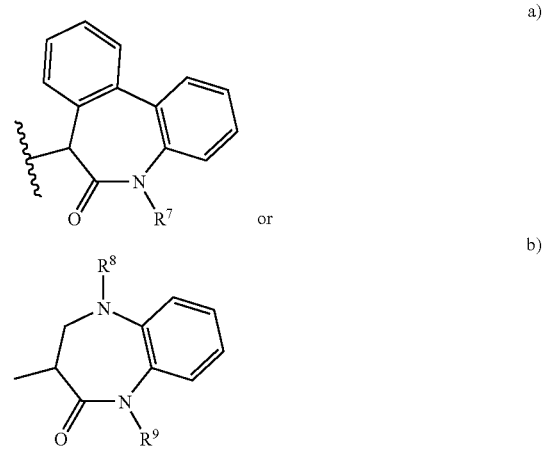

a)

or b)

and $R^1$, $R^2$, $R^3$, $R^7$, $R^8$, and $R^9$ are as defined in the specification and pharmaceutically acceptable salts, optically pure enantiomers, racemates or diastereomeric mixtures thereof. The compounds are useful for the treatment of Alzheimer's disease.

27 Claims, No Drawings

CARBAMIC ACID ALKYL ESTER DERIVATIVES

FIELD OF THE INVENTION

The invention relates to γ-secretase inhibitors and the treatment of Alzheimer's disease.

BACKGROUND OF THE INVENTION

Alzheimer's disease (AD) is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N— and C-termini, the main species are of 40 and 42 amino-acid length.

Abeta peptides are produced from APP through the sequential action of 2 proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. The majority of Abeta peptides is of 40 amino acids length (Aβ40), a minor species carries 2 additional amino acids at its C-terminus. Latter is supposed to be the more pathogenic amyloid peptide.

The β-secretase is a typical aspartyl protease. The γ-secretase has a proteolytic activity consisting of several proteins, its exact composition is incompletely understood. However, the presenilins are essential components of this activity and may represent a new group of atypical aspartyl proteases which cleave their substrates within the TM and which are themselves polytopic membrane proteins. Other essential components of γ-secretase are be nicastrin and the products of the aph1 and pen-2 genes. Proven substrates for γ-secretase are the APP and the proteins of the Notch receptor family, however, γ-secretase has a loose substrate specificity and may cleave further membrane proteins unrelated to APP and Notch.

The γ-secretase activity is absolutely required for the production of Abeta peptides. This has been shown both by genetic means, i.e., ablation of the presenilin genes and by low-molecular-weight inhibitory compounds. Since according to the amyloid hypothesis the production and deposition of Abeta is the ultimate cause for AD, it is thought that selective and potent inhibitors of γ-secretase will be useful for the prevention and treatment of AD.

Numerous documents describe the current knowledge on γ-secretase inhibition, for example the following publications:

Nature Reviews/Neuroscience, Vol. 3, April 2002/281,
Biochemical Society Transactions (2002), Vol. 30. part 4,
Current Topics in Medicinal Chemistry, 2002, 2, 371–383,
Current Medicinal Chemistry, 2002, Vol. 9, No. 11, 1087–1106,
Drug Development Research, 56, 211–227, 2002,
Drug Discovery Today, Vol. 6, No. 9, May 2001, 459–462,
FEBS Letters, 483, (2000), 6–10,
Science, Vol. 297, 353–356, July 2002 and
Journal of Medicinal Chemistry, Vol. 44, No. 13, 2001, 2039–2060.

SUMMARY OF THE INVENTION

The present invention provides compounds of formula I per se and pharmaceutically acceptable salts thereof. All forms of compounds of formula I, including optically pure enantiomers, racemates, and diastereomeric mixtures are provided in the present invention.

The present invention also provides compositions which contain a compound of formula I or a pharmaceutically acceptable salt thereof and a pharmaceutically acceptable carrier. The invention further provides methods for the manufacture of such compositions.

Compounds of formula I inhibit the activity γ-secretase. Thus, the present invention provides a method of inhibiting γ-secretase activity and a method for reducing or preventing the formation of various amyloidogenic Abeta peptides. The present invention further provides a method for the treatment, control, or prevention of Alzheimer's disease.

In particular, the present invention provides compounds of formula

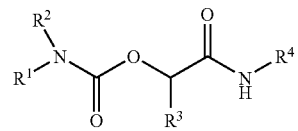

wherein
R$^1$ is —(CHR')$_q$-aryl or —(CHR')$_q$-heteroaryl, which is unsubstituted or mono, di- or tri-substituted by lower alkyl, lower alkoxy, CF$_3$ or halogen, or is lower alkyl, lower alkenyl, —(CH$_2$)$_n$—Si(CH$_3$)$_3$, —(CH$_2$)$_n$—O-lower alkyl, —(CH$_2$)$_n$—S-lower alkyl, —(CH$_2$)$_q$-cycloalkyl, or —(CH$_2$)$_n$—[CH(OH)]$_m$—(CF$_2$)$_p$—CH$_q$F$_{(3-q)}$, or is —(CH$_2$)$_n$—CR$_2$—CF$_3$, wherein the two R radicals form together with the carbon atom to which they are attached a cycloalkyl ring;

R' is hydrogen or lower alkyl;
n is 1,2 or 3;
m is 0 or 1;
p is 0, 1, 2, 3, 4, 5 or 6;
q is 0, 1, 2 or 3;
R$^2$ is hydrogen or lower alkyl;
R$^3$ is hydrogen, lower alkyl, —CH$_2$CF$_2$CF$_3$, CH$_2$CF$_3$, (CH$_2$)$_2$CF$_3$, CF$_3$, CHF$_2$, CH$_2$F, or is aryl optionally mono, di or tri-substituted by halogen, or is —(CH$_2$)$_n$NR$^5$R$^6$ wherein R$^5$ and R$^6$ are each independently selected from hydrogen or lower alkyl;

R⁴ is one of the following groups

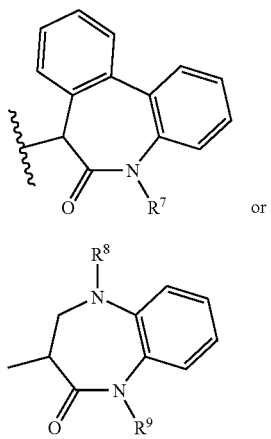

a)

b)

wherein
R⁷ is hydrogen, lower alkyl, —(CH₂)ₙ—CF₃ or —(CH₂)ₙ-cycloalkyl;
R⁸ is hydrogen, lower alkyl, —C(O)-phenyl, —C(O)-lower alkyl, —C(O)O—(CH₂)ₙ-cycloalkyl, —C(O)O—(CH₂)ₙ-lower alkyl, —C(O)NH—(CH₂)ₙ-lower alkyl or —C(O)NH—(CH₂)ₙ-cycloalkyl;
R⁹ is hydrogen, lower alkyl, —(CH₂)ₙ-cycloalkyl or —(CH₂)ₙ—CF₃;

or a pharmaceutically acceptable salt, optically pure enantiomer, racemate or diastereomeric mixture thereof.

It has been found that the compounds of general formula I are γ-secretase inhibitors and the related compounds may be useful in the treatment of Alzheimer's disease.

DETAILED DESCRIPTION OF THE INVENTION

The following definitions of general terms used herein apply irrespective of whether the terms in question appear alone or in combination. It must be noted that, as used in the specification and the appended claims, the singular forms "a," "an," and "the" include plural forms unless the context clearly indicates otherwise.

As used herein, the term "lower alkyl" denotes a saturated straight- or branched-chain alkyl group containing from 1 to 10 carbon atoms, for example, methyl, ethyl, propyl, isopropyl, n-butyl, i-butyl, 2-butyl, t-butyl and the like. Preferred lower alkyl groups are groups with 1–4 carbon atoms.

As used herein, the term "lower alkenyl" denotes a partially saturated straight- or branched-chain carbon group containing at least one double bond with 2 to 10 carbon atoms, for example ethenyl, but-2-enyl or 3,7-dimethyl-octa-2,6-dienyl.

The term "cycloalkyl" denotes a saturated carbocyclic group, containing 3–7 carbon atoms.

The term "lower alkoxy" denotes a group wherein the alkyl residues is as defined above, and which is attached via an oxygen atom.

The term "aryl" denotes a monovalent cyclic aromatic hydrocarbon radical consisting of one or more fused rings, in which at least one ring is aromatic in nature, for example phenyl or naphthyl.

The term "heteroaryl" denotes a monovalent heterocyclic aromatic radical, for example pyridyl, pyrazinyl, pyrimidinyl, triazinyl, thiazolyl, thiophenyl, furyl, pyrazol, pyrrolyl, imidazolyl or the like.

The term "halogen" denotes chlorine, iodine, fluorine and bromine.

The term "—(CH₂)ₙ—[CH(OH)]ₘ—(CF₂)ₚ—CH_qF_{(3-q)}" denotes a carbon chain, containing at least one halogen atom, for example —CH₂—CH₂—F, —CH₂—CF₃, —CH₂—CF₂—CF₃—, —CH₂—CH₂—CH₂—CF₃, —CH₂—CH₂—CF₂—CF₃, —CH₂—CH₂—CF₃—, —CH₂—CF₂—CF₂—CF₃, —CH₂—CH(OH)—CF₂—CF₂—CF₂—CF₃, or —CH₂—(CF₂)₆—CF₃.

The term "pharmaceutically acceptable," such as pharmaceutically acceptable carrier, excipient, etc. denotes pharmaceutically acceptable and substantially non-toxic to the subject to which the particular compound is administered.

The term "pharmaceutically acceptable salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" denotes an amount that is effective to prevent, alleviate, or ameliorate symptoms of disease or prolong the survival of the subject being treated.

"Amyloidogenic Abeta peptide reducing amount" denote the amount necessary to reduce the amount of amyloidogenic Abeta peptide present prior to administration of the compound.

The present invention provides compounds of formula I

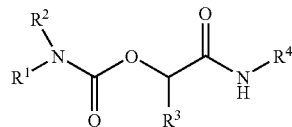

I wherein
R¹ is —(CHR')_q-aryl or —(CHR')_q-heteroaryl, which is unsubstituted or mono, di- or tri-substituted by lower alkyl, lower alkoxy, CF₃ or halogen, or is
lower alkyl, lower alkenyl, —(CH₂)ₙ—Si(CH₃)₃, —(CH₂)ₙ—O-lower alkyl, —(CH₂)ₙ—S-lower alkyl, —(CH₂)_q-cycloalkyl, or —(CH₂)ₙ—[CH(OH)]ₘ—(CF₂)ₚ—CH_qF_{(3-q)}, or is
—(CH₂)ₙ—CR₂—CF₃, wherein the two R radicals form together with the carbon atom to which they are attached a cycloalkyl ring;
R' is hydrogen or lower alkyl;
n is 1, 2 or 3;
m is 0 or 1;
p is 0, 1, 2, 3, 4, 5 or 6;
q is 0, 1, 2 or 3;
R² is hydrogen or lower alkyl;
R³ is hydrogen, lower alkyl, —CH₂CF₂CF₃, CH₂CF₃, (CH₂)₂CF₃, CF₃, CHF₂, CH₂F, or is aryl optionally mono, di or tri-substituted by halogen, or is —(CH₂)ₙNR⁵R⁶ wherein R⁵ and R⁶ are each independently selected from hydrogen or lower alkyl;

$R^4$ is one of the following groups

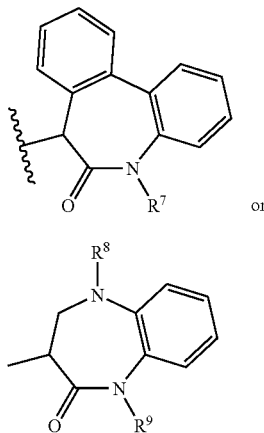

a)

b)

wherein
$R^7$ is hydrogen, lower alkyl, —$(CH_2)_n$—$CF_3$ or —$(CH_2)_n$-cycloalkyl;
$R^8$ is hydrogen, lower alkyl, —C(O)-phenyl, —C(O)-lower alkyl, —C(O)O—$(CH_2)_n$-cycloalkyl, —C(O)O—$(CH_2)_n$-lower alkyl, —C(O)NH—$(CH_2)_n$-lower alkyl or —C(O)NH—$(CH_2)_n$-cycloalkyl;
$R^9$ is hydrogen, lower alkyl, —$(CH_2)_n$-cycloalkyl or —$(CH_2)_n$—$CF_3$;
or a pharmaceutically acceptable salt, optically pure enantiomer, racemate or diastereomeric mixture thereof.

The most preferred compounds of formula I are those in which $R^4$ is a).

Especially preferred compounds from this group are those wherein $R^4$ is —$CH_2$-phenyl,
unsubstituted or mono, di- or tri-substituted by lower alkyl, lower alkoxy, $CF_3$ or halogen, for example the following compounds:
(2,3-difluoro-benzyl)-carbamic acid (S)-1-(5-methyl-6-oxo-6,7-dihydro-5H-dibenzo[b,d]azepin-7-ylcarbamoyl)-ethyl ester,
(2-trifluoromethyl-benzyl)-carbamic acid (S)-1-(5-methyl-6-oxo-6,7-dihydro-5H-dibenzo[b,d]azepin-7-ylcarbamoyl)-ethyl ester,
(2-methyl-benzyl)-carbamic acid (S)-1-(5-methyl-6-oxo-6,7-dihydro-5H-dibenzo[b,d]azepin-7-ylcarbamoyl)-ethyl ester,
(2,4-difluoro-benzyl)-carbamic acid (S)-1-(5-methyl-6-oxo-6,7-dihydro-5H-dibenzo[b,d]azepin-7-ylcarbamoyl)-ethyl ester,
(3,4-difluoro-benzyl)-carbamic acid (S)-1-(5-methyl-6-oxo-6,7-dihydro-5H-dibenzo[b,d]azepin-7-ylcarbamoyl)-ethyl ester,
(2,3,5-trifluoro-benzyl)-carbamic acid (S)-1-(5-methyl-6-oxo-6,7-dihydro-5H-dibenzo[b,d]azepin-7-ylcarbamoyl)-ethyl ester and
(2,3,6-trifluoro-benzyl)-carbamic acid (S)-1-(5-methyl-6-oxo-6,7-dihydro-5H-dibenzo[b,d]azepin-7-ylcarbamoyl)-ethyl ester.

Further preferred are those compounds wherein $R^4$ is a) and $R^1$ is —$(CH_2)_n$—[CH(OH)]$_m$—$(CF_2)_p$—$CH_qF_{(3-q)}$, for example the following compounds:
(2,2,2-trifluoro-ethyl)-carbamic acid (S)-1-(5-methyl-6-oxo-6,7-dihydro-5H-dibenzo[b,d]azepin-7-ylcarbamoyl)-ethyl ester, (2,2,3,3,3-pentafluoro-propyl)-carbamic acid (S)-1-(5-methyl-6-oxo-6,7-dihydro-5H-dibenzo[b,d]azepin-7-ylcarbamoyl)-ethyl ester,
(2,2,3,3,3-pentafluoro-propyl)-carbamic acid 2-fluoro-1-(5-methyl-6-oxo-6,7-dihydro-5H-dibenzo[b,d]azepin-7-ylcarbamoyl)-ethyl ester,
(2,2,3,3,3-pentafluoro-propyl)-carbamic acid 1-(5-methyl-6-oxo-6,7-dihydro-5H-dibenzo[b,d]azepin-7-ylcarbamoyl)-propyl ester,
(2,2,2-trifluoro-ethyl)-carbamic acid 1-(5-methyl-6-oxo-6,7-dihydro-5H-dibenzo[b,d]azepin-7-ylcarbamoyl)-propyl ester,
(2,2,2-trifluoro-ethyl)-carbamic acid 2-fluoro-1-(5-methyl-6-oxo-6,7-dihydro-5H-dibenzo[b,d]azepin-7-ylcarbamoyl)-ethyl ester,
(2,2,3,3,3-pentafluoro-propyl)-carbamic acid (S)-1-((S)-5-methyl-6-oxo-6,7-dihydro-5H-dibenzo[b,d]azepin-7-ylcarbamoyl)-ethyl ester,
(3,3,3-trifluoro-propyl)-carbamic acid (S)-1-((S)-5-methyl-6-oxo-6,7-dihydro-5H-dibenzo[b,d]azepin-7-ylcarbamoyl)-ethyl ester,
(3,3,4,4-pentafluoro-butyl)-carbamic acid (S)-1-((S)-5-methyl-6-oxo-6,7-dihydro-5H-dibenzo[b,d]azepin-7-ylcarbamoyl)-ethyl ester,
(2,2,3,3,4,4,4-heptafluoro-butyl)-carbamic acid (S)-1-((S)-5-methyl-6-oxo-6,7-dihydro-5H-dibenzo[b,d]azepin-7-ylcarbamoyl)-ethyl ester,
(2,2,3,3,4,4,5,5,6,6,7,7,8,8,8-pentadecafluoro-octyl)-carbamic acid (S)-1-((S)-5-methyl-6-oxo-6,7-dihydro-5H-dibenzo[b,d]azepin-7-ylcarbamoyl)-ethyl ester,
(2,2,2-trifluoro-ethyl)-carbamic acid (S)-1-((S)-5-methyl-6-oxo-6,7-dihydro-5H-dibenzo[b,d]azepin-7-ylcarbamoyl)-ethyl ester,
(2,2,3,3,3-pentafluoro-propyl)-carbamic acid (S)-1-((S)-6-oxo-6,7-dihydro-5H-dibenzo[b,d]azepin-7-ylcarbamoyl)-ethyl ester,
(3,3,3-trifluoro-propyl)-carbamic acid (S)-1-((S)-6-oxo-6,7-dihydro-5H-dibenzo[b,d]azepin-7-ylcarbamoyl)-ethyl ester,
(2,2,3,3,3-pentafluoro-propyl)-carbamic acid (S)-1-((S)-5-cyclopropylmethyl-6-oxo-6,7-dihydro-5H-dibenzo[b,d]azepin-7-ylcarbamoyl)-ethyl ester and
(2,2,3,3,3-pentafluoro-propyl)-carbamic acid (S)-1-[(S)-6-oxo-5-(2,2,2-trifluoroethyl)-6,7-dihydro-5H-dibenzo[b,d]azepin-7-ylcarbamoyl]-ethyl ester.

Preferred are further compounds of formula I wherein $R^4$ is a) and $R^1$ is —$(CH_2)_n$-cycloalkyl, for example the following compound:
cyclopropylmethyl-carbamic acid 3-methyl-1-(5-methyl-6-oxo-6,7-dihydro-5H-dibenzo[b,d]azepin-7-ylcarbamoyl)-butyl ester.

Further preferred are compounds of formula I wherein $R^4$ is a) and $R^1$ is —$(CH_2)_n$—$CR_2$—$CF_3$, wherein the two R radicals form together with the carbon atom a cycloalkyl ring, for example the following compound:
(1-trifluoromethyl-cyclopropylmethyl)-carbamic acid (S)-1-(5-methyl-6-oxo-6,7-dihydro-5H-dibenzo[b,d]azepin-7-ylcarbamoyl)-ethyl ester.

Further preferred are those compounds wherein $R^4$ is a) and $R^1$ is lower alkyl, for example the following compound:
(3,3-dimethyl-butyl)-carbamic acid (S)-1-((S)-5-methyl-6-oxo-6,7-dihydro-5H-dibenzo[b,d]azepin-7-ylcarbamoyl)-ethyl ester.

Preferred are also compounds of formula I wherein $R^4$ is b). Compounds in the group are for example (2,2,3,3,3-pentafluoro-propyl)-carbamic acid (S)-1-((S)-5-benzoyl-1-methyl-2-oxo-2,3,4,5-tetrahydro-1H-benzo[b][1,4]diazepin-3-ylcarbamoyl)-ethyl ester (2,2,3,3,3-pentafluoro-propyl)-carbamic acid (S)-1-((S)-5-acetyl-1-methyl-2-oxo-2,3,4,5-tetrahydro-1H-benzo[b][1,4]diazepin-3-ylcarbamoyl)-ethyl ester (S)-5-methyl-4-oxo-3-[(S)-2-(2,2,3,3,3-pentafluoro-propylcarbamoyloxy)-propionylamino]-2,3,4,5-tetrahydro-benzo[b][1,4]diazepine-1-carboxylic acid cyclopropylmethyl ester and (2,2,3,3,3-pentafluoro-propyl)-carbamic acid (S)-1-[(S)-5-(cyclopropylmethyl-carbamoyl)-2-oxo-1-(2,2,2-trifluoro-ethyl)-2,3,4,5-tetrahydro-1H-benzo[b][1,4]diazepin-3-ylcarbamoyl]-ethyl ester.

One embodiment of the present invention provides compounds of formula I-1,

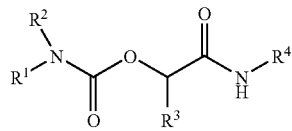

I-1 wherein $R^1$ is $—(CH_2)_n$-aryl or $—(CH_2)_n$-heteroaryl, which is unsubstituted or mono, di- or tri-substituted by lower alkyl, lower alkoxy, $CF_3$ or halogen, or is lower alkyl, $—(CH_2)_n—O$-lower alkyl, $—(CH_2)_n—S$-lower alkyl, $—(CH_2)_n$-cycloalkyl, $—(CH_2)_nCH_2F$, $—(CH_2)_n—CF_3$, $—(CH_2)_n—CF_2—CF_3$, or $—(CH_2)_n—CF_2—CHF_2$, or is $—(CH_2)_n—CR_2—CF_3$, wherein the two R radicals form together with the carbon atom to which they are attached a cycloalkyl ring;

$R^2$ is hydrogen or lower alkyl;

$R^3$ is hydrogen, lower alkyl, $—CH_2F$, $CHF_2$, $CF_3$, aryl optionally mono, di or tri-substituted by halogen, or is $—(CH_2)_nNR^5R^6$, wherein $R^5$ and $R^6$ are independently from each other hydrogen or lower alkyl;

$R^4$ is one of the following groups a)

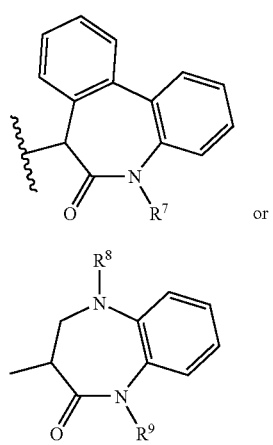

or b)

wherein $R^7$ is lower alkyl or $—(CH)_2$-cycloalkyl;

$R^8$, $R^9$ are each independently hydrogen, lower alkyl, $—(CH_2)_n$-cycloalkyl or $—C(O)$—phenyl;

or a pharmaceutically acceptable salt, optically pure enantiomer, racemate or diastereomeric mixture thereof.

The present compounds of formula I and their pharmaceutically acceptable salts can be prepared by methods known in the art, for example, by processes described below, which processes comprise a) reacting a compound of formula

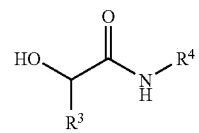

IV with a compound of formula

R¹NCO    III to produce a compound of formula

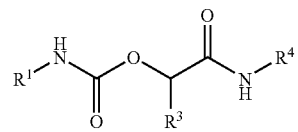

Ia wherein $R^1$—$R^4$ have the meaning as described above, or b) reacting a compound of formula

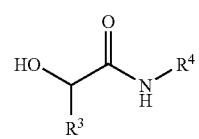

IV with a compound of formula

NHR¹R²    II in the presence of a suitable phosgene equivalent, such as 4-nitrophenyl chloroformate, and a base, such as triethylamine, to produce a compound of formula

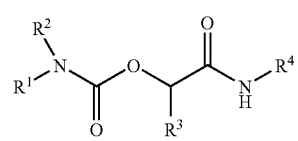

I wherein $R^1$—$R^4$ have the meaning as described above, and if desired, converting the compounds obtained into pharmaceutically acceptable acid addition salts.

The detailed description can be found below and in Examples 1–83. The starting materials of formula V and VI are known compounds or may be prepared by methods well-known in the art.

Scheme 1

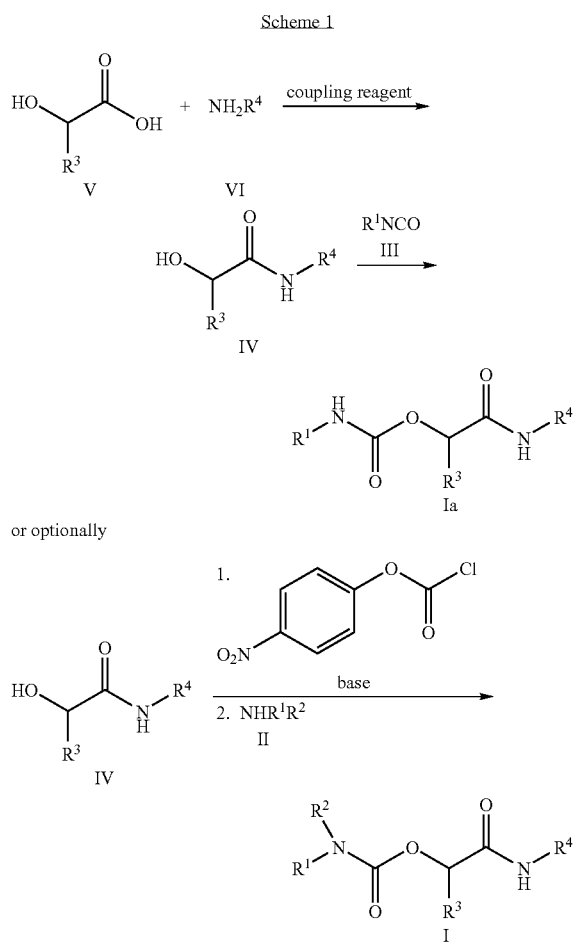

In this scheme $R^1$ to $R^4$ are as described above.

In accordance with scheme 1 a compound of formula I may be prepared as follows: An hydroxy-acid of formula V is suitably activated, for instance with a coupling agent such as EDC (1-(3-dimethylaminopropyl)-3-ethylcarbodiimide), and converted with an amine of formula VI to an intermediate hydroxy compound of formula IV. This can be transformed into a compound of formula Ia by reaction with an isocyanate of formula III. Optionally, a compound of formula IV can be transformed into a compound of formula I by reaction with a suitable phosgene equivalent and a base, such as 4-nitrophenyl chloroformate and triethylamine, and an amine of formula II.

Several compounds of formula I may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically acceptable salts possess valuable pharmacological properties. Specifically, it has been found that the compounds of the present invention can inhibit γ-secretase.

The compounds were investigated in accordance with the test given hereinafter.

Description of γ-secretase Assay

The activity of test compounds can be evaluated in assays which measure the proteolytic cleavage of suitable substrates by γ-secretase activity. These can be cellular assays where e.g., a substrate of the γ-secretase is fused in its cytoplasmic domain to a transcription factor. Cells are transfected with this fusion gene and a reporter gene, e.g., firefly luciferase, which expression is enhanced by the transcription factor. Cleavage of the fused substrate by γ-secretase will lead to expression of the reporter gene which can be monitored in appropriate assays. The γ-secretase activity can also be determined in a cellular assay where e.g. HEK293 cells are transfected with a vector which expresses the cDNA for the human APP and which secrete Abeta peptides into the culture medium. The amount of secreted peptides can be determined with specific ELISA assays. Cell lines of neuronal origin secrete Abeta peptides from their endogenous APP gene which can be measured with the specific ELISA assay. Treatment with compounds which inhibit γ-secretase leads to a reduction of secreted Abeta thus providing a measure of inhibition.

A cell-free assay of γ-secretase activity uses a HEK293 membrane fraction as a source of γ-secretase and a recombinant APP substrate. Latter consist of the C-terminal 100 amino acids of human APP fused to a 6× Histidin tail for purification which is expressed in E.coli in a regulatable expression vector, e.g. pEt15. This recombinant protein corresponds to the truncated APP fragment which results after γ-secretase cleavage of the extracellular domain and which constitutes the γ-secretase substrate. The assay principle is described in Li Y M et al, PNAS 97(11), 6138–6143 (2000). Hek293 cells are mechanically disrupted and the microsomal fraction is isolated by differential centrifugation. The membranes are solubilized in detergent (0.25% CHAPSO) and incubated with the APP substrate. The Abeta peptides which are produced by γ-secretase cleavage of the substrate are detected by specific ELISA assays as described (Brockhaus M et al, Neuroreport 9(7), 1481–1486 (1998).

The preferred compounds show an $IC_{50} < 0.1$ μM (cell-free assay). In the list below are described some data to the γ-secretase inhibition:

| Example No. | $IC_{50}$ [μM] |
| --- | --- |
| 18 | 0.099 |
| 20 | 0.037 |
| 22 | 0.011 |
| 23 | 0.096 |

-continued

| Example No. | IC$_{50}$ [μM] |
|---|---|
| 25 | 0.066 |
| 27 | 0.079 |
| 28 | 0.069 |
| 29 | 0.018 |
| 30 | 0.085 |
| 39 | 0.03 |
| 40 | 0.021 |
| 43 | 0.062 |
| 45 | 0.09 |
| 49 | 0.04 |
| 51 | 0.04 |
| 61 | 0.004 |
| 63 | 0.008 |
| 64 | 0.002 |
| 65 | 0.005 |
| 67 | 0.071 |
| 68 | 0.070 |
| 73 | 0.059 |
| 80 | 0.001 |
| 81 | 0.009 |
| 82 | 0.006 |
| 83 | 0.002 |

The present invention also provides pharmaceutical compositions containing one or more compound of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositoriesor injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable salts thereof and, if desired, one or more other therapeutically valuable substances into a galienical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injectable solutions.

Compounds of the present invention are inhibitors of γ-secretase. As such, they are useful for the I control or prevention of illnesses based on the inhibition of the γ-secretase, such as of Alzheimer's disease. Thus, the present invention also provides a method of the treatment of Alzheimer's disease which comprises administering to a patient an effective amount of a compound of formula I or a pharmaceutically acceptable salt thereof. The present invention further provides a method of the treatment of Alzheimer's disease which comprises administering to a patient an effective amount of a compound of formula I-1 or a pharmaceutically acceptable salt thereof. The present invention also provides a method for the inhibition, reduction, or prevention of amyloidogenic Abeta peptides.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

Mix items 1, 2 and 3 in a suitable mixer for 30 minutes.
2. Add items 4 and 5 and mix for 3 minutes.
3. Fill into a suitable capsule.

EXAMPLE 1

Benzyl-carbamic acid (S)-1-(5-methyl-6-oxo-6,7-dihydro-5H-dibenzo[b,d]azepin-7-ylcarbamoyl)-ethyl ester

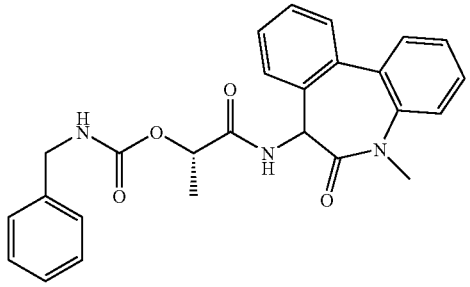

a) (S)-2-Hydroxy-N-(5-methyl-6-oxo-6,7-dihydro-5H-dibenzo[b,d]azepin-7-yl)-propionamide Hydroxybenzotriazole (344 mg, 2.55 mmol), diisopropylethylamine (659 mg, 5.1 mmol) and 1-(3-dimethylaminopropyl)-3-ethylcarbodiimide hydrochloride (488 mg, 2.55 mmol) were added to a cooled (0° C.) solution of 7-amino-5-methyl-5H,7H-dibenzo[b,d]azepin-6-one hydrochloride (700 mg, 2.55 mmol) and L-(+)-lactic acid (252 mg, 2.8 mmol) in THF (7 ml) and stirred overnight at r.t. The solvent was evaporated, the residue was taken up in dichloromethane and washed with water. The organic phase was dried over $Na_2SO_4$ and evaporated. Upon chromatographic purification (silica gel, dichloromethane/methanol=1:0–9:1) the title compound (820 mg, quant.) was obtained as a white solid.

b) Benzyl-carbamic acid (S)-1-(5-methyl-6-oxo-6,7-dihydro-5H-dibenzo[b,d]azepin-7-ylcarbamoyl)-ethyl ester Benzylisocyanate (13.3 mg, 0.1 mmol) was added to a solution of (S)-2-hydroxy-N-(5-methyl-6-oxo-6,7-dihydro-5H-dibenzo[b,d]azepin-7-yl)-propionamide (30 mg, 0.1 mmol) in Toluol (1 ml) and heated to 100° C. for 1 week. The solvent was evaporated and the residue was dissolved in DMF (0.5 ml). The title compound, MS: m/e=444.4 (M+H$^+$) (29 mg, 67%), was isolated from this mixture by automated, preparative HPLC (YMC CombiPrep C18 column 50×20 mm, solvent gradient 5–95% $CH_3CN$ in 0.1% TFA(aq) over 6.0 min, λ=230 nm, flow rate 30 ml/min).

EXAMPLE 2

Tolyl-carbamic acid (S)-1-(5-methyl-6-oxo-6,7-dihydro-5H-dibenzo[b,d]azepin-7-ylcarbamoyl)-ethyl ester

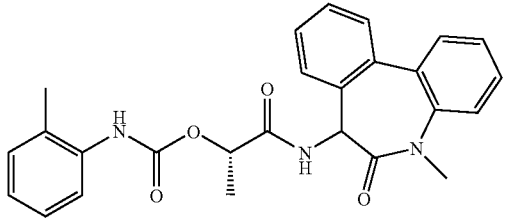

The title compound, MS: m/e=444.4 (M+H$^+$), was prepared in analogy to example 1 from o-tolyl isocyanate.

EXAMPLE 3

(4-Fluoro-phenyl)-carbamic acid (S)-1-(5-methyl-6-oxo-6,7-dihydro-5H-dibenzo[b,d]azepin-7-ylcarbamoyl)-ethyl ester

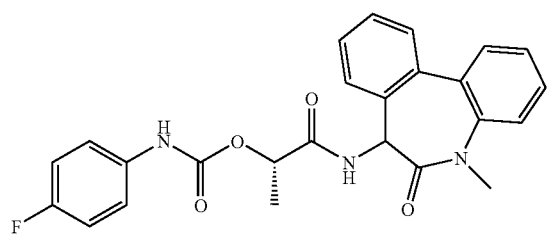

The title compound, MS: m/e=448.3 (M+H$^+$), was prepared in analogy to example 1 from 4-fluorophenyl isocyanate.

EXAMPLE 4

(3-Fluoro-phenyl)-carbamic acid (S)-1-(5-methyl-6-oxo-6,7-dihydro-5H-dibenzo[b,d]azepin-7-ylcarbamoyl)-ethyl ester

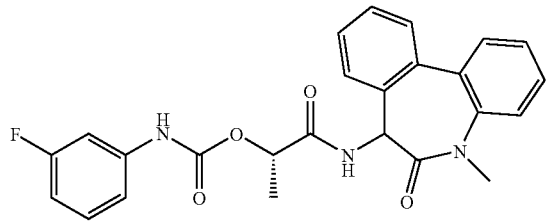

The title compound, MS: m/e=448.3 (M+H$^+$), was prepared in analogy to example 1 from 3-fluorophenyl isocyanate.

EXAMPLE 5

Thiophen-2-yl-carbamic acid (S)-1-(5-methyl-6-oxo-6,7-dihydro-5H-dibenzo[b,d]azepin-7-ylcarbamoyl)-ethyl ester

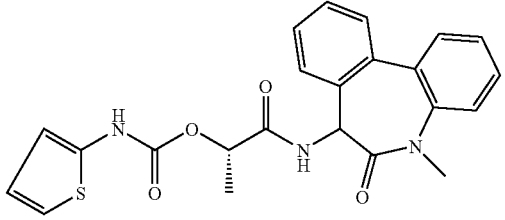

The title compound, MS: m/e=436.3 (M+H$^+$), was prepared in analogy to example 1 from 2-thienyl isocyanate.

EXAMPLE 6

Ethyl-carbamic acid (S)-1-(5-methyl-6-oxo-6,7-dihydro-5H-dibenzo[b,d]azepin-7-ylcarbamoyl)-ethyl ester

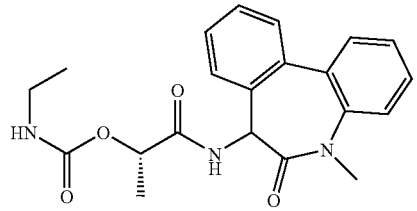

A solution of (S)-2-hydroxy-N-(5-methyl-6-oxo-6,7-dihydro-5H-dibenzo[b,d]azepin-7-yl)-propionamide (30 mg, 0.09 mmol), 4-nitrophenyl chloroformate (19 mg, 0.09 mmol), and triethylamine (20 microliter) in toluol (1 ml) were shaken overnight at r.t. Ethylamine hydrochloride (7.9 mg, 0.1 mmol) was added and the mixture was shaken again overnight at r.t. The solvent was evaporated and the residue was dissolved in DMF (0.5 ml). The title compound, MS: m/e=382.3 (M+H$^+$), (11 mg, 30%) was isolated from this mixture by automated, preparative HPLC (YMC CombiPrep C18 column 50×20 mm, solvent gradient 5–95% CH$_3$CN in 0.1% TFA(aq) over 6.0 min, λ=230 nm, flow rate 30 ml/min).

EXAMPLE 7

(2-Methoxy-ethyl)-carbamic acid (S)-1-(5-methyl-6-oxo-6,7-dihydro-5H-dibenzo[b,d]azepin-7-ylcarbamoyl)-ethyl ester

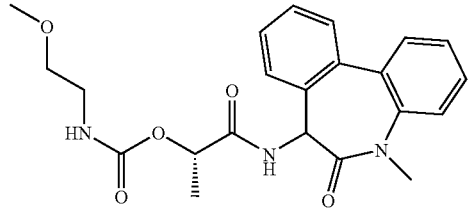

The title compound, MS: m/e=412.3 (M+H$^+$), was prepared in analogy to example 6 from 2-methoxyethylamine.

EXAMPLE 8

Propyl-carbamic acid (S)-1-(5-methyl-6-oxo-6,7-dihydro-5H-dibenzo[b,d]azepin-7-ylcarbamoyl)-ethyl ester

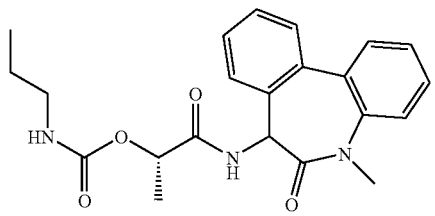

The title compound, MS: m/e=396.4 (M+H$^+$), was prepared in analogy to example 6 from propylamine.

EXAMPLE 9

Cyclopropylmethyl-carbamic acid (S)-1-(5-methyl-6-oxo-6,7-dihydro-5H-dibenzo[b,d]azepin-7-ylcarbamoyl)-ethyl ester

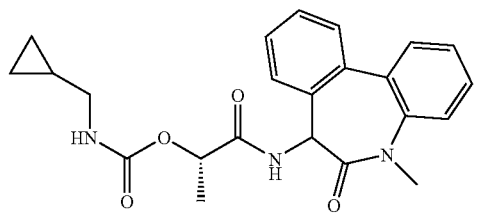

The title compound, MS: m/e=408.4 (M+H$^+$), was prepared in analogy to example 6 from aminomethylcyclopropane.

EXAMPLE 10

(2-Methylsulfanyl-ethyl)-carbamic acid (S)-1-(5-methyl-6-oxo-6,7-dihydro-5H-dibenzo[b,d]azepin-7-ylcarbamoyl)-ethyl ester

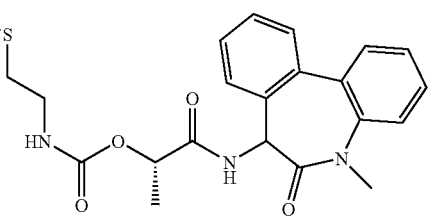

The title compound, MS: m/e=428.5 (M+H$^+$), was prepared in analogy to example 6 from 2-(methylthio)ethylamine.

EXAMPLE 11

(3-Methoxy-propyl)-carbamic acid (S)-1-(5-methyl-6-oxo-6,7-dihydro-5H-dibenzo[b,d]azepin-7-ylcarbamoyl)-ethyl ester

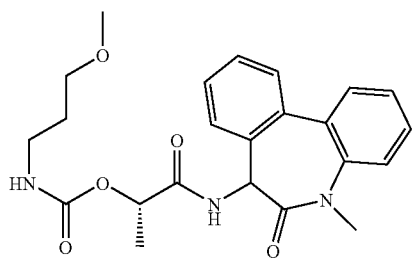

The title compound, MS: m/e=426.4 (M+H$^+$), was prepared in analogy to example 6 from 3-methoxypropylamine.

EXAMPLE 12

Cyclopropyl-carbamic acid (S)-1-(5-methyl-6-oxo-6,7-dihydro-5H-dibenzo[b,d]azepin-7-ylcarbamoyl)-ethyl ester

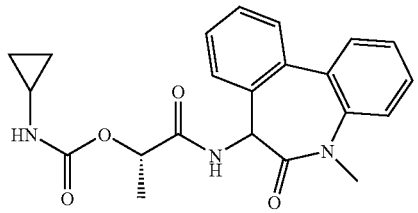

The title compound, MS: m/e=394.3 (M+H⁺), was prepared in analogy to example 6 from cyclopropylamine.

EXAMPLE 13

Isopropyl-carbamic acid (S)-1-(5-methyl-6-oxo-6,7-dihydro-5H-dibenzo[b,d]azepin-7-ylcarbamoyl)-ethyl ester

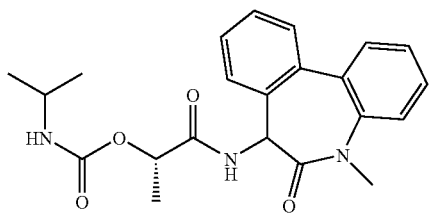

The title compound, MS: m/e=396.4 (M+H⁺), was prepared in analogy to example 6 from isopropylamine.

EXAMPLE 14

(2-Fluoro-ethyl)-carbamic acid (S)-1-(5-methyl-6-oxo-6,7-dihydro-5H-dibenzo[b,d]azepin-7-ylcarbamoyl)-ethyl ester

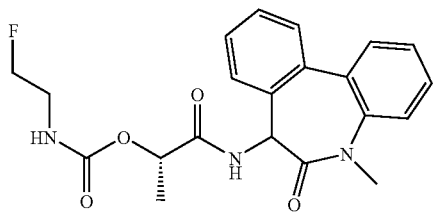

The title compound, MS: m/e=400.5 (M+H⁺), was prepared in analogy to example 6 from 2-fluoroethylamine hydrochloride.

EXAMPLE 15

(4-Fluoro-benzyl)-carbamic acid (S)-1-(5-methyl-6-oxo-6,7-dihydro-5H-dibenzo[b,d]azepin-7-ylcarbamoyl)-ethyl ester

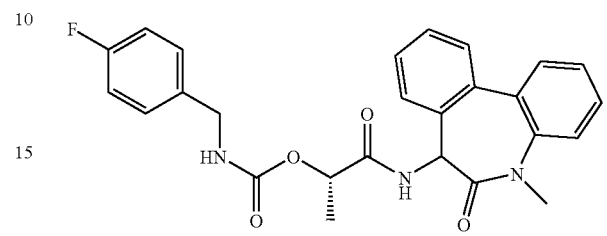

The title compound, MS: m/e=462.3 (M+H⁺), was prepared in analogy to example 6 from 4-fluorobenzylamine.

EXAMPLE 16

(2-Fluoro-benzyl)-carbamic acid (S)-1-(5-methyl-6-oxo-6,7-dihydro-5H-dibenzo[b,d]azepin-7-ylcarbamoyl)-ethyl ester

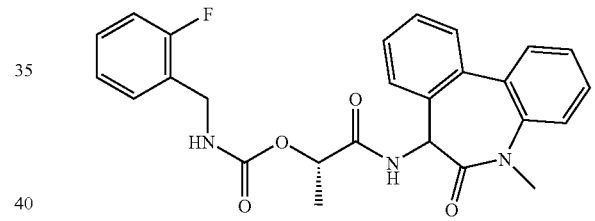

The title compound, MS: m/e=462.3 (M+H⁺), was prepared in analogy to example 6 from 2-fluorobenzylamine.

EXAMPLE 17

(2,5-Difluoro-benzyl)-carbamic acid (S)-1-(5-methyl-6-oxo-6,7-dihydro-5H-dibenzo[b,d]azepin-7-ylcarbamoyl)-ethyl ester

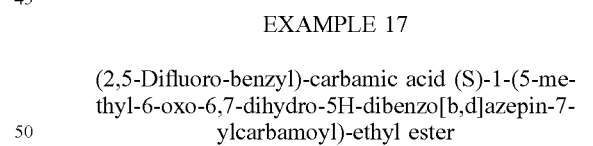

The title compound, MS: m/e=479.17 (M+H⁺), was prepared in analogy to example 6 from 2,5-difluorobenzylamine.

EXAMPLE 18

(2,3-Difluoro-benzyl)-carbamic acid (S)-1-(5-methyl-6-oxo-6,7-dihydro-5H-dibenzo[b,d]azepin-7-ylcarbamoyl)-ethyl ester

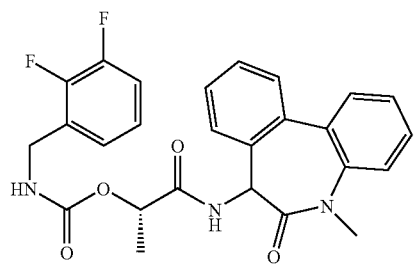

The title compound, MS: m/e=480.4 (M+H⁺), was prepared in analogy to example 6 from 2,3-difluorobenzylamine.

EXAMPLE 19

[2-(3-Fluoro-phenyl)-ethyl]-carbamic acid (S)-1-(5-methyl-6-oxo-6,7-dihydro-5H-dibenzo[b,d]azepin-7-ylcarbamoyl)-ethyl ester

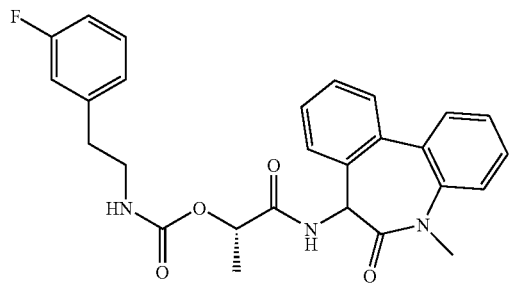

The title compound, MS: m/e=476.3 (M+H⁺), was prepared in analogy to example 6 from 3-fluorophenethylamine.

EXAMPLE 20

(2,2,2-Trifluoro-ethyl)-carbamic acid (S)-1-(5-methyl-6-oxo-6,7-dihydro-5H-dibenzo[b,d]azepin-7-ylcarbamoyl)-ethyl ester

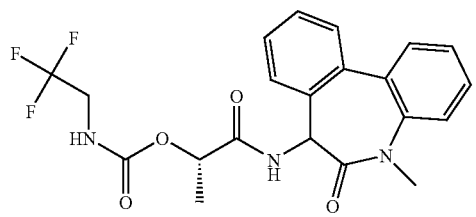

The title compound, MS: m/e=436.4 (M+H⁺), was prepared in analogy to example 6 from 2,2,2-trifluoroethylamine.

EXAMPLE 21

(3,5-Difluoro-benzyl)-carbamic acid (S)-1-(5-methyl-6-oxo-6,7-dihydro-5H-dibenzo[b,d]azepin-7-ylcarbamoyl)-ethyl ester

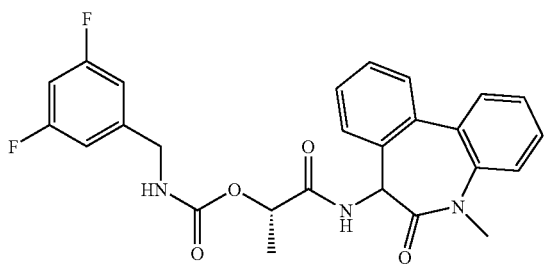

The title compound, MS: m/e=480.4 (M+H⁺), was prepared in analogy to example 6 from 3,5-difluorobenzylamine.

EXAMPLE 22

(2,2,3,3,3-Pentafluoro-propyl)-carbamic acid (S)-1-(5-methyl-6-oxo-6,7-dihydro-5H-dibenzo[b,d]azepin-7-ylcarbamoyl)-ethyl ester

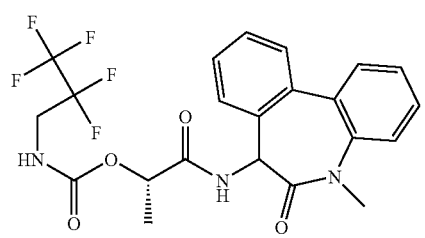

The title compound, MS: m/e=486.4 (M+H⁺), was prepared in analogy to example 6 from 2,2,3,3,3-pentafluoropropylamine.

EXAMPLE 23

(2-Trifluoromethyl-benzyl)-carbamic acid (S)-1-(5-methyl-6-oxo-6,7-dihydro-5H-dibenzo[b,d]azepin-7-ylcarbamoyl)-ethyl ester

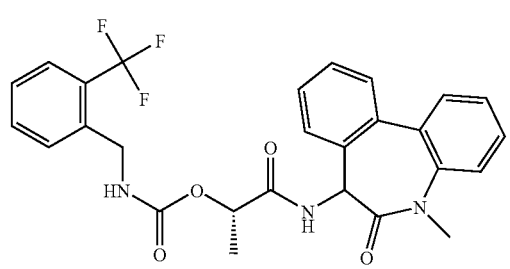

The title compound, MS: m/e=512.3 (M+H⁺), was prepared in analogy to example 6 from 2-(trifluoromethyl)benzylamine.

EXAMPLE 24

(2-Chloro-benzyl)-carbamic acid (S)-1-(5-methyl-6-oxo-6,7-dihydro-5H-dibenzo[b,d]azepin-7-ylcarbamoyl)-ethyl ester

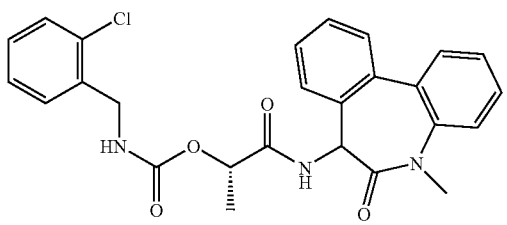

The title compound, MS: m/e=478.1 (M+H⁺), was prepared in analogy to example 6 from 2-chlorobenzylamine.

EXAMPLE 25

(2-Methyl-benzyl)-carbamic acid (S)-1-(5-methyl-6-oxo-6,7-dihydro-5H-dibenzo[b,d]azepin-7-ylcarbamoyl)-ethyl ester

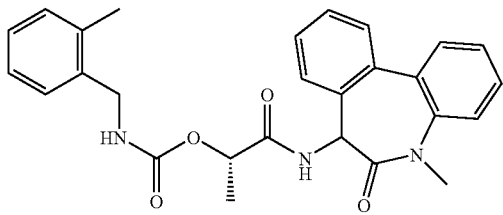

The title compound, MS: m/e=458.3 (M+H⁺), was prepared in analogy to example 6 from 2-methylbenzylamine.

EXAMPLE 26

(2-Methoxy-benzyl)-carbamic acid (S)-1-(5-methyl-6-oxo-6,7-dihydro-5H-dibenzo[b,d]azepin-7-ylcarbamoyl)-ethyl ester

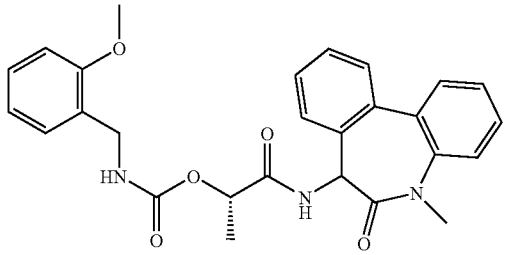

The title compound, MS: m/e=474.2 (M+H⁺), was prepared in analogy to example 6 from 2-methoxybenzylamine.

EXAMPLE 27

(2,4-Difluoro-benzyl)-carbamic acid (S)-1-(5-methyl-6-oxo-6,7-dihydro-5H-dibenzo[b,d]azepin-7-ylcarbamoyl)-ethyl ester

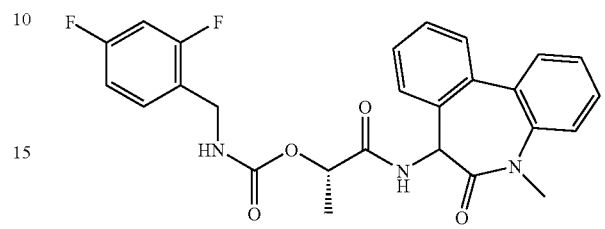

The title compound, MS: m/e=480.2 (M+H⁺), was prepared in analogy to example 6 from 2,4-difluorobenzylamine.

EXAMPLE 28

(3,4-Difluoro-benzyl)-carbamic acid (S)-1-(5-methyl-6-oxo-6,7-dihydro-5H-dibenzo[b,d]azepin-7-ylcarbamoyl)-ethyl ester

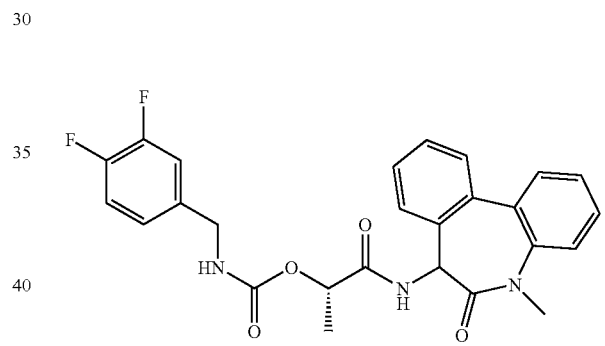

The title compound, MS: m/e=480.2 (M+H⁺), was prepared in analogy to example 6 from 3,4-difluorobenzylamine.

EXAMPLE 29

(2,3,5-Trifluoro-benzyl)-carbamic acid (S)-1-(5-methyl-6-oxo-6,7-dihydro-5H-dibenzo[b,d]azepin-7-ylcarbamoyl)-ethyl ester

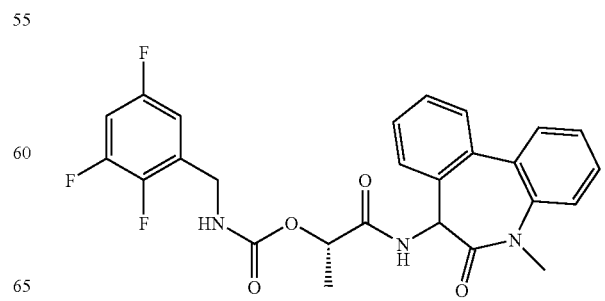

The title compound, MS: m/e=498.2 (M+H⁺), was prepared in analogy to example 6 from 2,3,5-trifluorobenzylamine.

EXAMPLE 30

(2,3,6-Trifluoro-benzyl)-carbamic acid (S)-1-(5-methyl-6-oxo-6,7-dihydro-5H-dibenzo[b,d]azepin-7-ylcarbamoyl)-ethyl ester

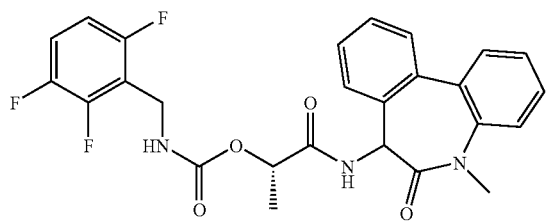

The title compound, MS: m/e=498.2 (M+H⁺), was prepared in analogy to example 6 from 2,3,6-trifluorobenzylamine.

EXAMPLE 31

(2-Fluoro-5-trifluoromethyl-benzyl)-carbamic acid (S)-1-(5-methyl-6-oxo-6,7-dihydro-5H-dibenzo[b,d]azepin-7-ylcarbamoyl)-ethyl ester

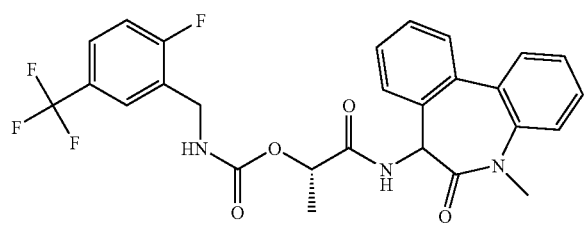

The title compound, MS: m/e=530.1 (M+H⁺), was prepared in analogy to example 6 from 2-fluoro-5-(trifluoromethyl)benzylamine.

EXAMPLE 32

(2,6-Difluoro-benzyl)-carbamic acid (S)-1-(5-methyl-6-oxo-6,7-dihydro-5H-dibenzo[b,d]azepin-7-ylcarbamoyl)-ethyl ester

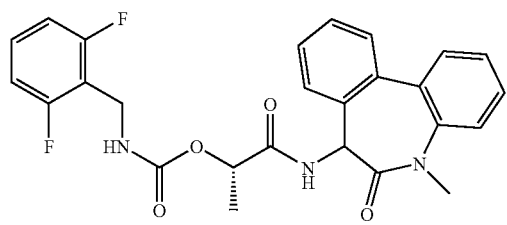

The title compound, MS: m/e=480.2 (M+H⁺), was prepared in analogy to example 6 from 2,6-difluorobenzylamine.

EXAMPLE 33

((R)-1-Phenyl-ethyl)-carbamic acid (S)-1-(5-methyl-6-oxo-6,7-dihydro-5H-dibenzo[b,d]azepin-7-ylcarbamoyl)-ethyl ester

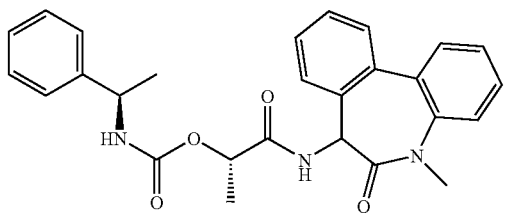

The title compound, MS: m/e=458.3 (M+H⁺), was prepared in analogy to example 6 from (R)-1-phenylethylamine.

EXAMPLE 34

((S)-1-Phenyl-ethyl)-carbamic acid (S)-1-(5-methyl-6-oxo-6,7-dihydro-5H-dibenzo[b,d]azepin-7-ylcarbamoyl)-ethyl ester

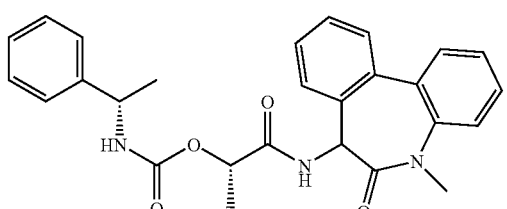

The title compound, MS: m/e=458.3 (M+H⁺), was prepared in analogy to example 6 from (S)-1-phenylethylamine.

EXAMPLE 35

Benzyl-methyl-carbamic acid (S)-1-(5-methyl-6-oxo-6,7-dihydro-5H-dibenzo[b,d]azepin-7-ylcarbamoyl)-ethyl ester

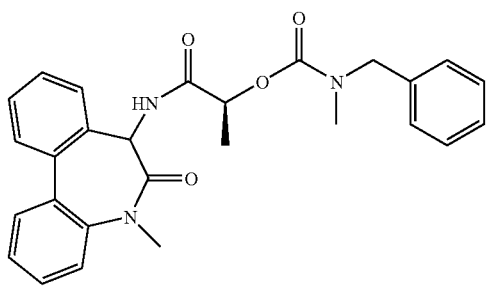

The title compound, MS: m/e=458.2 (M+H⁺), was prepared in analogy to example 6 from N-methylbenzylamine.

EXAMPLE 36

(2,2,3,3,3-Pentafluoro-propyl)-carbamic acid (R)-1-(5-methyl-6-oxo-6,7-dihydro-5H-dibenzo[b,d]azepin-7-ylcarbamoyl)-ethyl ester

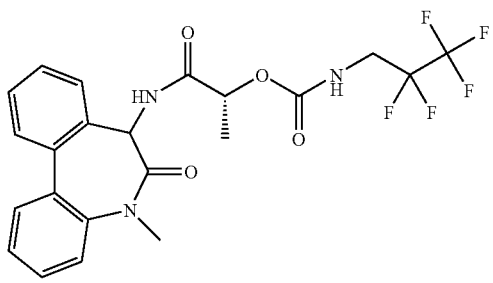

The title compound, MS: m/e=486.2 (M+H$^+$), was prepared in analogy to example 6 from 2,2,3,3,3-pentafluoro-propylamine and (S)-2-hydroxy-N-(5-methyl-6-oxo-6,7-dihydro-5H-dibenzo[b,d]azepin-7-yl)-propionamide. The latter can be obtained in analogy to (S)-2-hydroxy-N-(5-methyl-6-oxo-6,7-dihydro-5H-dibenzo[b,d]azepin-7-yl)-propionamide (example 1, step a) from D-(−)-Lactic acid.

EXAMPLE 37

(2,2,3,3,3-Pentafluoro-propyl)-carbamic acid 3-methyl-(S)-1-(5-methyl-6-oxo-6,7-dihydro-5H-dibenzo[b,d]azepin-7-ylcarbamoyl)-butyl ester

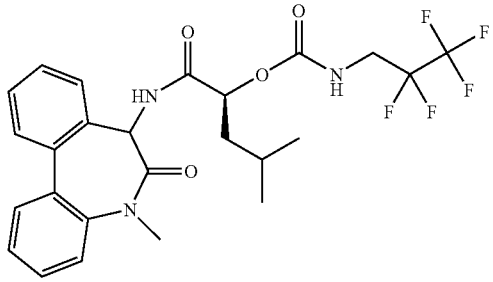

The title compound, MS: m/e=518.5 (M+H$^+$), was prepared in analogy to example 6 from 2,2,3,3,3-pentafluoro-propylamine and (S)-2-hydroxy-4-methyl-pentanoic acid (5-methyl-6-oxo-6,7-dihydro-5H-dibenzo[b,d]azepin-7-yl)-amide. The latter can be obtained in analogy to (S)-2-hydroxy-N-(5-methyl-6-oxo-6,7-dihydro-5H-dibenzo[b,d]azepin-7-yl)-propionamide (example 1, step a) from (S)-2-hydroxy-4-methyl-pentanoic acid.

EXAMPLE 38

Benzyl-carbamic acid 3-methyl-(S)-1-(5-methyl-6-oxo-6,7-dihydro-5H-dibenzo[b,d]azepin-7-ylcarbamoyl)-butyl ester

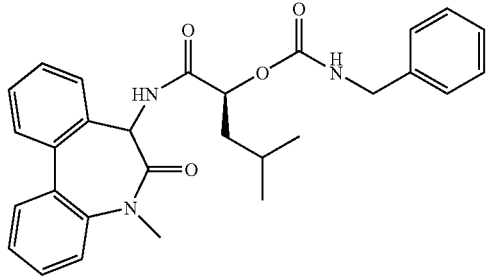

The title compound, MS: m/e=484.4 (M+H$^+$), was prepared in analogy to example 37 from benzylamine.

EXAMPLE 39

(2,2,3,3,3-Pentafluoro-propyl)-carbamic acid 2-fluoro-1-(5-methyl-6-oxo-6,7-dihydro-5H-dibenzo[b,d]azepin-7-ylcarbamoyl)-ethyl ester

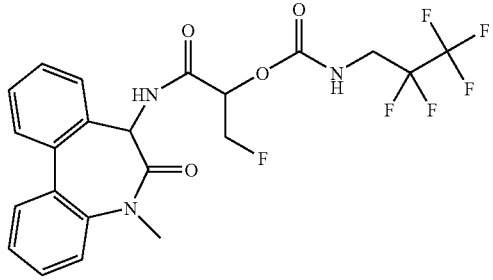

The title compound, MS: m/e=504.1 (M+H$^+$), was prepared in analogy to example 6 from 2,2,3,3,3-pentafluoro-propylamine and 3-fluoro-2-hydroxy-N-(5-methyl-6-oxo-6,7-dihydro-5H-dibenzo[b,d]azepin-7-yl)-propionamide. The latter can be obtained in analogy to (S)-2-hydroxy-N-(5-methyl-6-oxo-6,7-dihydro-5H-dibenzo[b,d]azepin-7-yl)-propionamide (example 1, step a) from 3-fluoro lactic acid.

EXAMPLE 40

(2,2,3,3,3-Pentafluoro-propyl)-carbamic acid 1-(5-methyl-6-oxo-6,7-dihydro-5H-dibenzo[b,d]azepin-7-ylcarbamoyl)-propyl ester

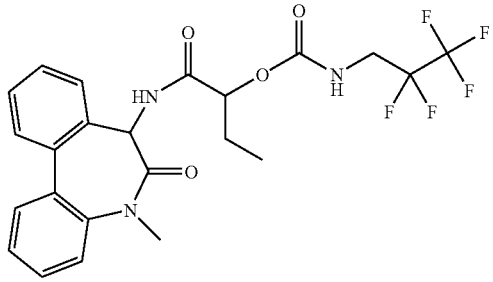

The title compound, MS: m/e=500.2 (M+H$^+$), was prepared in analogy to example 6 from 2,2,3,3,3-pentafluoro-propylamine and 2-hydroxy-N-(5-methyl-6-oxo-6,7-dihydro-5H-dibenzo[b,d]azepin-7-yl)-butyramide. The latter can be obtained in analogy to (S)-2-hydroxy-N-(5-methyl-6-oxo-6,7-dihydro-5H-dibenzo[b,d]azepin-7-yl)-propionamide (example 1, step a) from 2-hydroxy-butyric acid.

EXAMPLE 41

(2,2,3,3,3-Pentafluoro-propyl)-carbamic acid 2-dimethylamino-1-(5-methyl-6-oxo-6,7-dihydro-5H-dibenzo[b,d]azepin-7-ylcarbamoyl)-ethyl ester

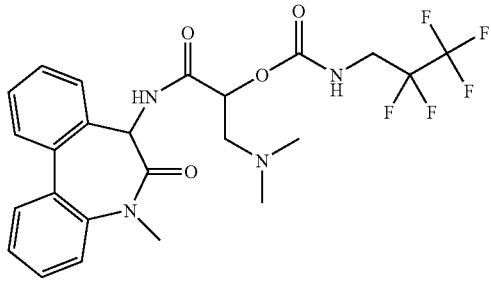

The title compound, MS: m/e=529.2 (M+H⁺), was prepared in analogy to example 6 from 2,2,3,3,3-pentafluoropropylamine and 3-dimethylamino-2-hydroxy-N-(5-methyl-6-oxo-6,7-dihydro-5H-dibenzo[b,d]azepin-7-yl)-propionamide. The latter can be obtained in analogy to (S)-2-hydroxy-N-(5-methyl-6-oxo-6,7-dihydro-5H-dibenzo[b,d]azepin-7-yl)-propionamide (example 1, step a) from 3-dimethylamino-2-hydroxy-propionic acid.

EXAMPLE 42

Cyclopropylmethyl-carbamic acid (5-methyl-6-oxo-6,7-dihydro-5H-dibenzo[b,d]azepin-7-ylcarbamoyl)-methyl ester

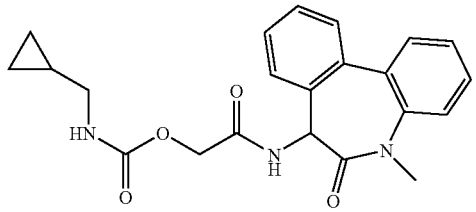

The title compound, MS: m/e=394.1 (M+H⁺), was prepared in analogy to example 6 from cyclopropylmethylamine and 2-hydroxy-N-(5-methyl-6-oxo-6,7-dihydro-5H-dibenzo[b,d]azepin-7-yl)-acetamide. The latter can be obtained in analogy to (S)-2-Hydroxy-N-(5-methyl-6-oxo-6,7-dihydro-5H-dibenzo[b,d]azepin-7-yl)-propionamide (example 1, step a) from hydroxy-acetic acid.

EXAMPLE 43

Cyclopropylmethyl-carbamic acid 3-methyl-1-(5-methyl-6-oxo-6,7-dihydro-5H-dibenzo[b,d]azepin-7-ylcarbamoyl)-butyl ester

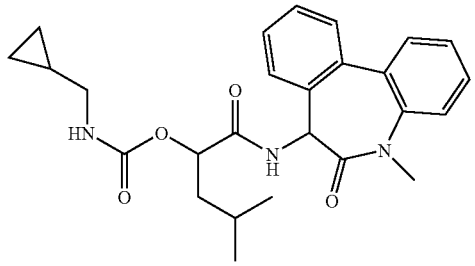

The title compound, MS: m/e=450.3 (M+H⁺), was prepared in analogy to example 6 from cyclopropylmethylamine and 2-hydroxy-4-methyl-pentanoic acid (5-methyl-6-oxo-6,7-dihydro-5H-dibenzo[b,d]azepin-7-yl)-amide. The latter can be obtained in analogy to (S)-2-hydroxy-N-(5-methyl-6-oxo-6,7-dihydro-5H-dibenzo[b,d]azepin-7-yl)-propionamide (example 1, step a) from 2-hydroxy-4-methyl-pentanoic acid.

EXAMPLE 44

Cyclopropylmethyl-carbamic acid (3,5-difluoro-phenyl)-(5-methyl-6-oxo-6,7-dihydro-5H-dibenzo[b,d]azepin-7-ylcarbamoyl)-methyl ester

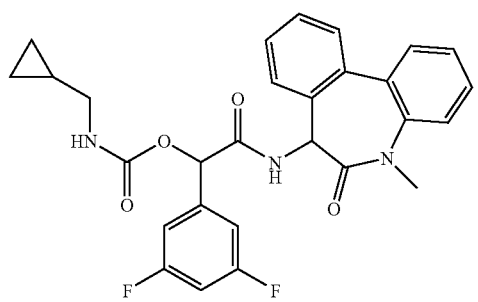

The title compound, MS: m/e=506.2 (M+H⁺), was prepared in analogy to example 6 from cyclopropylmethylamine and 2-(3,5-difluoro-phenyl)-2-hydroxy-N-(5-methyl-6-oxo-6,7-dihydro-5H-dibenzo[b,d]azepin-7-yl)-acetamide. The latter can be obtained in analogy to (S)-2-hydroxy-N-(5-methyl-6-oxo-6,7-dihydro-5H-dibenzo[b,d]azepin-7-yl)-propionamide (example 1, step a) from (3,5-difluoro-phenyl)-hydroxy-acetic acid.

EXAMPLE 45

Trifluoromethyl-cyclopropylmethyl)-carbamic acid (S)-1-(5-methyl-6-oxo-6,7-dihydro-5H-dibenzo[b,d]azepin-7-ylcarbamoyl)-ethyl ester

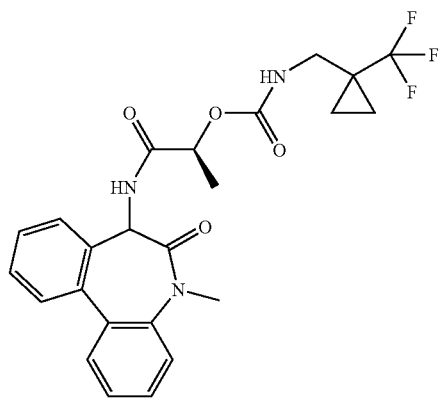

The title compound, MS: m/e=476.4 (M+H⁺), was prepared in analogy to example 6 from 1-trifluoromethyl-cyclopropylmethylamine.

EXAMPLE 46

(4,4,4-Trifluoro-butyl)-carbamic acid (S)-1-(5-methyl-6-oxo-6,7-dihydro-5H-dibenzo[b,d]azepin-7-ylcarbamoyl)-ethyl ester

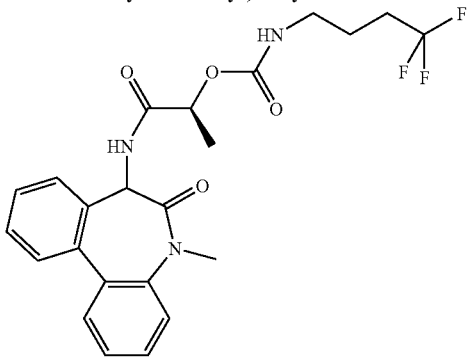

The title compound, MS: m/e=464.5 (M+H$^+$), was prepared in analogy to example 6 from 4,4,4-trifluoro-butylamine.

EXAMPLE 47

(3,3,4,4-Tetrafluoro-butyl)-carbamic acid (S)-1-(5-methyl-6-oxo-6,7-dihydro-5H-dibenzo[b,d]azepin-7-ylcarbamoyl)-ethyl ester

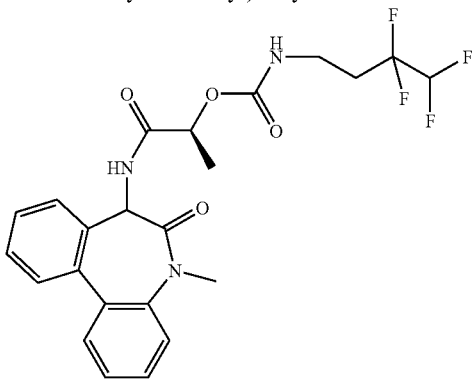

The title compound, MS: m/e=482.5 (M+H$^+$), was prepared in analogy to example 6 from 3,3,4,4-tetrafluoro-butylamine.

EXAMPLE 48

(3,3,4,4-Tetrafluoro-butyl)-carbamic acid 1-(5-methyl-6-oxo-6,7-dihydro-5H-dibenzo[b,d]azepin-7-ylcarbamoyl)-propyl ester

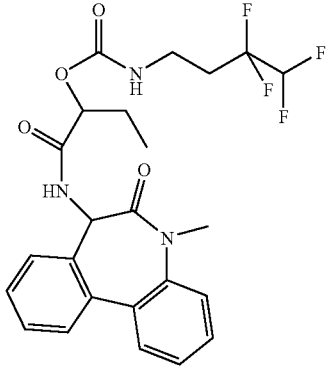

The title compound, MS: m/e=496.5 (M+H$^+$), was prepared in analogy to example 6 from 3,3,4,4-tetrafluoro-butylamine and 2-hydroxy-N-(5-methyl-6-oxo-6,7-dihydro-5H-dibenzo[b,d]azepin-7-yl)-butyramide. The latter can be obtained in analogy to (S)-2-hydroxy-N-(5-methyl-6-oxo-6,7-dihydro-5H-dibenzo[b,d]azepin-7-yl)-propionamide (example 1, step a) from hydroxybutyric acid.

EXAMPLE 49

(2,2,2-Trifluoro-ethyl)-carbamic acid 1-(5-methyl-6-oxo-6,7-dihydro-5H-dibenzo[b,d]azepin-7-ylcarbamoyl)-propyl ester

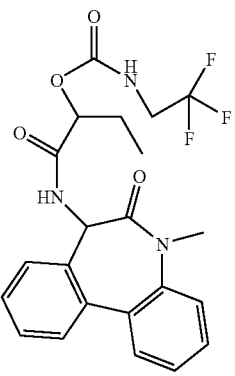

The title compound, MS: m/e=450.6 (M+H$^+$), was prepared in analogy to example 6 from 2,2,2-trifluoro-ethylamine and 2-Hydroxy-N-(5-methyl-6-oxo-6,7-dihydro-5H-dibenzo[b,d]azepin-7-yl)-butyramide. The latter can be obtained in analogy to (S)-2-hydroxy-N-(5-methyl-6-oxo-6,7-dihydro-5H-dibenzo[b,d]azepin-7-yl)-propionamide (example 1, step a) from hydroxybutyric acid.

EXAMPLE 50

(3,3,4,4-Tetrafluoro-butyl)-carbamic acid 2-fluoro-1-(5-methyl-6-oxo-6,7-dihydro-5H-dibenzo[b,d]azepin-7-ylcarbamoyl)-ethyl ester

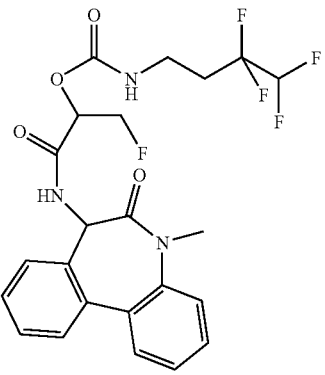

The title compound, MS: m/e=500.5 (M+H$^+$), was prepared in analogy to example 6 from 3,3,4,4-tetrafluoro-butylamine and 3-fluoro-2-hydroxy-N-(5-methyl-6-oxo-6,7-dihydro-5H-dibenzo[b,d]azepin-7-yl)-propionamide. The latter can be obtained in analogy to (S)-2-hydroxy-N-(5-methyl-6-oxo-6,7-dihydro-5H-dibenzo[b,d]azepin-7-yl)-propionamide (example 1, step a) from 3-fluoro-lactic acid.

EXAMPLE 51

(2,2,2-Trifluoro-ethyl)-carbamic acid 2-fluoro-1-(5-methyl-6-oxo-6,7-dihydro-5H-dibenzo[b,d]azepin-7-ylcarbamoyl)-ethyl ester

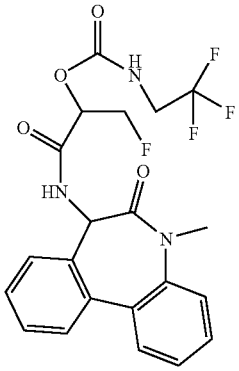

The title compound, MS: m/e=454.5 (M+H⁺), was prepared in analogy to example 6 from 2,2,2-trifluoro-ethyl and 3-fluoro-2-hydroxy-N-(5-methyl-6-oxo-6,7-dihydro-5H-dibenzo[b,d]azepin-7-yl)-propionamide. The latter can be obtained in analogy to (S)-2-hydroxy-N-(5-methyl-6-oxo-6,7-dihydro-5H-dibenzo[b,d]azepin-7-yl)-propionamide (example 1, step a) from 3-fluoro-lactic acid.

EXAMPLE 52

Trifluoromethyl-cyclopropylmethyl)-carbamic acid 2-fluoro-1-(5-methyl-6-oxo-6,7-dihydro-5H-dibenzo[b,d]azepin-7-ylcarbamoyl)-ethyl ester

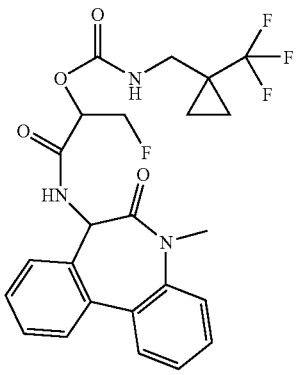

The title compound, MS: m/e=494.5 (M+H⁺), was prepared in analogy to example 6 from 1-trifluoromethyl-cyclopropylmethylamine and 3-fluoro-2-hydroxy-N-(5-methyl-6-oxo-6,7-dihydro-5H-dibenzo[b,d]azepin-7-yl)-propionamide. The latter can be obtained in analogy to (S)-2-hydroxy-N-(5-methyl-6-oxo-6,7-dihydro-5H-dibenzo[b,d]azepin-7-yl)-propionamide (example 1, step a) from 3-fluoro-lactic acid.

EXAMPLE 53

(2,2,3,3,3-Pentafluoro-propyl)-carbamic acid (S)-1-((S)-1-cyclopropylmethyl-5-methyl-2-oxo-2,3,4,5-tetrahydro-1H-benzo[b,d][1,4]diazepin-3-ylcarbamoyl)-ethyl ester

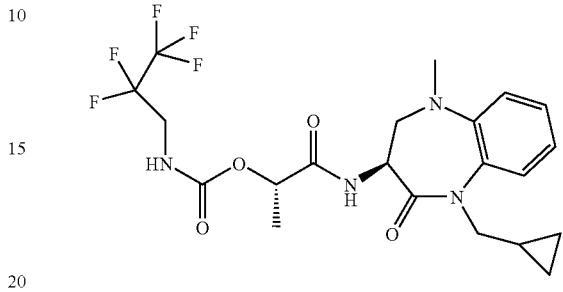

a) ((S)-1-Cyclopropylmethyl-2-oxo-2,3,4,5-tetrahydro-1H-benzo[b][1,4]diazepin-3-yl)-carbamic acid tert-butyl ester To a solution of 0.6 g (2.2 mmol) (S)-(2-oxo-2,3,4,5-tetrahydro-1H-benzo[b][1,4]diazepin-3-yl)-carbamic acid tert-butyl ester in 10 ml of tetrahydrofuran at −75° C. 2.2 ml (2.2 mmol) of lithium bis(trimethylsilyl)amide solution (1M in tetrahydrofurane) was added. After stirring for 30 min at −75° C. the mixture was allowed to reach room temperature and 0.35 g (2.6 mmol) of bromomethyl-cyclopropane was added. The mixture was stirred for 2.5 hours at room temperature and concentrated in vacuo. The residue was distributed between 1M NaHSO₄ solution and ethyl acetate. The combined organic layers were re-extracted with water and dried (MgSO₄) to yield 0.285 g (40%) of ((S)-1-cyclopropylmethyl-2-oxo-2,3,4,5-tetrahydro-1H-benzo[b][1,4]diazepin-3-yl)-carbamic acid tert-butyl ester.

b) (S)-3-Amino-1-cyclopropyl-5-methyl-1,3,4,5-tetrahydro-benzo[b][1,4]diazepin-2-one To 0.35 g (1 mmol) of ((S)-1-cyclopropylmethyl-2-oxo-2,3,4,5-tetrahydro-1H-benzo[b][1,4]diazepin-3-yl)-carbamic acid tert-butyl ester in dimethylformamide (3.5 ml) 0.36 g (3.0 mmol) of potassium carbonate and 0.37 g (3 mmol) of methyl iodide were added and the mixture was stirred at room temperature overnight. Water (10 ml) was added and the mixture was extracted two times with ethyl acetate (10 ml each). The combined organic layers were dried (MgSO₄) and purified by column chromatography (hexane/ethyl acetate=1:1) to yield 0.33 g (72%) of a white solid. This compound was dissolved in a mixture of 2 ml of dichlorometane and 2 ml of trifluoracetic acid and stirred for 2.5 h at room temperature. For workup the mixture was concentrated in vacuo, then dichloromethane was added and the mixture was extracted with sodium bicarbonate solution. The organic phase was dried (MgSO₄) and evaporated to yield 0.22 g of (S)-3-amino-1-cyclopropyl-5-methyl-1,3,4,5-tetrahydro-benzo[b][1,4]diazepin-2-one.

c) (S)—N—((S)-1-Cyclopropylmethyl-5-methyl-2-oxo-2,3,4,5-tetrahydro-1H-benzo[b][1,4]diazepin-3-yl)-2-hydroxy-propionamide Hydroxybenzotriazole (121 mg, 1 mmol), diisopropylethylamine (23 2 mg, 2 mmol) and 1-(3-dimethylaminopropyl)-3-ethylcarbodiimide hydrochloride (172 mg, 1 mmol) were added to a cooled (0° C.) solution of (S)-3-amino-1-cyclopropyl-5-methyl-1,3,4,5-tetrahydro-benzo[b][1,4]diazepin-2-one (220 mg, 1 mmol) and L-(+)-lactic acid (81 mg, 1 mmol) in THF (2 ml) and stirred overnight at r.t. The solvent was evaporated, the residue was taken up in dichloromethane and washed with water. The organic phase was dried over Na$_2$SO$_4$ and evaporated. Upon chromatographic purification (silica gel, dichloromethane/methanol=1:0–9:1) the title compound (347 mg, quant.) was obtained as a white solid.

d) (2,2,3,3,3-Pentafluoro-propyl)-carbamic acid (S)-1-((S)-1-cyclopropylmethyl-5-methyl-2-oxo-2,3,4,5-tetrahydro-1H-benzo[b][1,4]diazepin-3-ylcarbamoyl)-ethyl ester The title compound, MS: m/e=493.3 (M+H$^+$), was prepared in analogy to example 6 from 2,2,3,3,3-pentafluoropropylamine and (S)—N—((S)-1-cyclopropylmethyl-5-methyl-2-oxo-2,3,4,5-tetrahydro-1H-benzo[b][1,4]diazepin-3-yl)-2-hydroxy-propionamide.

EXAMPLE 54

(2,2,2-Trifluoro-ethyl)-carbamic acid (S)-1-cyclopropylmethyl-5-methyl-2-oxo-2,3,4,5-tetrahydro-1H-benzo[b][1,4]diazepin-3-ylcarbamoyl)-ethyl ester

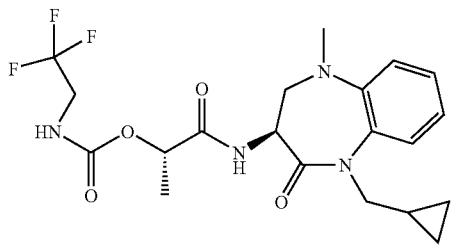

The title compound, MS: m/e=483.3 (M+H$^+$), was prepared in analogy to example 56 from 2,2,2-trifluoro-ethylamine.

EXAMPLE 55

Trifluoromethyl-cyclopropylmethyl)-carbamic acid (S)-1-((S)-1-cyclopropylmethyl-5-methyl-2-oxo-2,3,4,5-tetrahydro-1H-benzo[b][1,4]diazepin-3-ylcarbamoyl)-ethyl ester

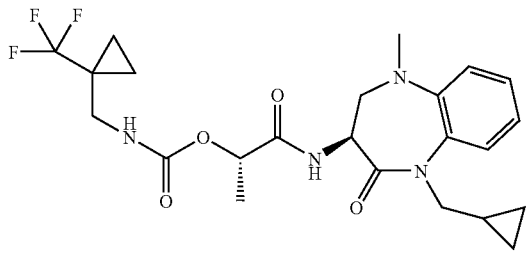

The title compound, MS: m/e=443.1 (M+H$^+$), was prepared in analogy to example 56 from 1-trifluoromethyl-cyclopropylmethylamine.

EXAMPLE 56

(2,2,3,3,3-Pentafluoro-propyl)-carbamic acid (S)-1-((S)-5-benzoyl-1-methyl-2-oxo-2,3,4,5-tetrahydro-1H-benzo[b][1,4]diazepin-3-ylcarbamoyl)-ethyl ester

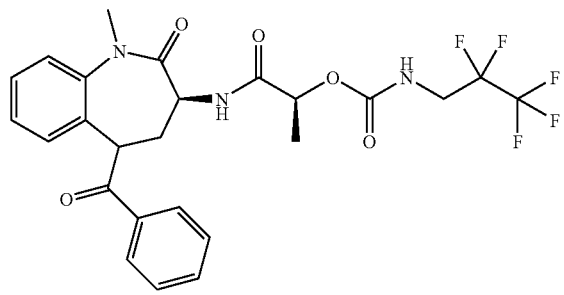

a) (S)-(-1-Methyl-2-oxo-2,3,4,5-tetrahydro-1H-benzo[b][1,4]diazepin-3-yl)-carbamic acid tert-butyl ester To a solution of 5.0 g (18 mmol) (S)-(2-oxo-2,3,4,5-tetrahydro-1H-benzo[b][1,4]diazepin-3-yl)-carbamic acid tert-butyl ester in 80 ml of tetrahydrofuran at −75° C. 18 ml (18 mmol) of lithium bis(trimethylsilyl)amide solution (1M in tetrahydrofurane) was added. After stirring for 30 min at −75° C. the mixture was allowed to reach room temperature and 3.07 g (21.6 mmol) of methyl iodide was added. The mixture was stirred for 2.5 hours at room temperature and concentrated in vacuo. The residue was distributed between 1M NaHSO$_4$ solution and ethyl acetate. The combined organic layers were reextracted with water and dried (MgSO$_4$). After evaporation of the solvent, (S)-(1-methyl-2-oxo-2,3,4,5-tetrahydro-1H-benzo[b][1,4]diazepin-3-yl)-carbamic acid tert-butyl ester was obtained in sufficient purity for the next step.

b) (S)-(5-Benzoyl-1-methyl-2-oxo-2,3,4,5-tetrahydro-1H-benzo[b][1,4]diazepin-3-yl)-carbamic acid tert-butyl ester (S)-(1-Methyl-2-oxo-2,3,4,5-tetrahydro-1H-benzo[b][1,4]diazepin-3-yl)-carbamic acid tert-butyl ester (260 mg, 0.55 mmol), triethylamine (111 mg, 1.1 mmol), and benzoyl chloride (93 mg, 0.66 mmol) were dissolved in dichloromethane (2 ml) and stirred overnight. The reaction mixture was then poured on HCl (1N), and extracted with dichloromethane. The organic layer was washed with NaHCO$_3$ (1N), dried, and evaporated. (S)-(5-Benzoyl-1-methyl-2-oxo-2,3,4,5-tetrahydro-1H-benzo[b][1,4]diazepin-3-yl)-carbamic acid tert-butyl ester was obtained in sufficient purity for the next step.

c) (S)-3-Amino-5-benzoyl-1-methyl-1,3,4,5-tetrahydro-benzo[b][1,4]diazepin-2-one (S)-(5-Benzoyl-1-methyl-2-oxo-2,3,4,5-tetrahydro-1H-benzo[b][1,4]diazepin-3-yl)-carbamic acid tert-butyl ester (260 mg, 0.66 mmol) was dissolved in a mixture of trifluoroacetic acid and dichloromethane (1:1, 2 ml) for 2.5 h. Upon evaporation of the volatile parts, (S)-3-amino-5-benzoyl-1-methyl-1,3,4,5-tetrahydro-benzo[b][1,4]diazepin-2-one was obtained in sufficient purity for the next step.

d) (2,2,3,3,3-Pentafluoro-propyl)-carbamic acid (S)-1-((S)-5-benzoyl-1-methyl-2-oxo-2,3,4,5-tetrahydro-1H-benzo[b][1,4]diazepin-3-ylcarbamoyl)-ethyl ester The title compound, MS: m/e=543.2 (M+H$^+$), was prepared in analogy to example 53 from 2,2,3,3,3-pentafluoropropylamine and N—((S)-5-benzoyl-1-methyl-2-oxo-2,3,4,5-tetrahydro-1H-benzo[b][1,4]diazepin-3-yl)-(S)-2-hydroxy-propionamide. The latter can be prepared in analogy to (S)-2-hydroxy-N-(5-methyl-6-oxo-6,7-dihydro-5H-dibenzo[b,d]azepin-7-yl)-propionamide (example 1, step a) from (S)-3-amino-5-benzoyl-1-methyl-1,3,4,5-tetrahydro-benzo[b][1,4]diazepin-2-one.

EXAMPLE 57

(2,2,3,3,3-Pentafluoro-propyl)-carbamic acid (S)-1-((S)-5-acetyl-1-methyl-2-oxo-2,3,4,5-tetrahydro-1H-benzo[b][1,4]diazepin-3-ylcarbamoyl)-ethyl ester

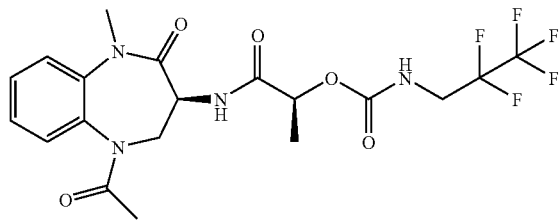

a) ((S)-5-Acetyl-1-methyl-2-oxo-2,3,4,5-tetrahydro-1H-benzo[b][1,4]diazepin-3-yl)-carbamic acid tert-butyl ester In an analogous manner to that described in Example 56 b), the acylation of (S)-(1-methyl-2-oxo-2,3,4,5-tetrahydro-1H-benzo[b][1,4]diazepin-3-yl)-carbamic acid tert-butyl ester [Example 56 a)] with acetic acid anhydride yielded the title compound as a white solid; MS: m/e=334 (M+H)$^+$.

b) (S)-5-Acetyl-3-amino-1-methyl-1,3,4,5-tetrahydro-benzo[b][1.4]diazepin-2-one hydrochloride In an analogous manner to that described in Example 56 c), the cleavage of the tert-butoxycarbonyl group of the ((S)-5-acetyl-1-methyl-2-oxo-2,3,4,5-tetrahydro-1H-benzo[b][1,4]diazepin-3-yl)-carbamic acid tert-butyl ester yielded the title compound as a light yellow solid which was engaged in the next step without further purification; MS: m/e=234 (M+H)$^+$.

c) (S)—N—((S)-5-Acetyl-1-methyl-2-oxo-2,3,4,5-tetrahydro-1H-benzo[b][1,4]diazepin-3-yl)-2-hydroxy-propionamide In an analogous manner to that described in Example 53 c), the condensation of (S)-5-acetyl-3-amino-1-methyl-1,3,4,5-tetrahydro-benzo[b][1,4]diazepin-2-one hydrochloride with L-(+)-lactic acid yielded the title compound as a yellow foam; MS: m/e=306 (M+H)$^+$.

d) (2,2,3,3,3-Pentafluoro-propyl)-carbamic acid (S)-1-((S)-5-acetyl-1-methyl-2-oxo-2,3,4,5-tetrahydro-1H-benzo[b][1,4]diazepin-3-ylcarbamoyl)-ethyl ester A solution of 50 mg (0.16 mmol) of (S)—N—((S)-5-acetyl-1-methyl-2-oxo-2,3,4,5-tetrahydro-1H-benzo[b][1,4]diazepin-3-yl)-2-hydroxy-propionamide in 1.5 ml of pyridine was treated with 39 mg (0.18 mmol) of 4-nitrophenyl chloroformate, and the mixture was stirred at room temperature for 18 h. For the working-up, the solvent was evaporated and the residue chromatographed on silica gel using a 3:1-mixture of heptane and ethyl acetate as the eluent. There were obtained 31 mg (40% of theory) of carbonic acid (S)-1-((S)-5-acetyl-1-methyl-2-oxo-2,3,4,5-tetrahydro-1H-benzo[b][1,4]diazepin-3-ylcarbamoyl)-ethyl ester 4-nitrophenyl ester; MS: m/e=488 (M+NH$_4$)$^+$. The ester was treated with 0.7 ml of 2,2,3,3,3-pentafluoro-propylamine and the mixture was stirred at room temperature for 36 h. For the working-up, 3 ml of ethyl acetate were added and the solution was washed with a saturated solution of sodium carbonate and a saturated solution of sodium chloride. The organic layer was dried over sodium sulphate and evaporated under reduced pressure. For purification, the crude product was chromatographed on silica gel using a gradient of a 98:2- to 95:5-mixture of dichloromethane and methanol as the eluent. There were obtained 12 mg (38% of theory) of the title compound as a white solid; MS: m/e=498 (M+NH$_4$)$^+$.

EXAMPLE 58

(2,3,5-Trifluoro-benzyl)-carbamic acid (S)-1-((S)-5-acetyl-1-methyl-2-oxo-2,3,4,5-tetrahydro-1H-benzo[b][1,4]diazepin-3-ylcarbamoyl)-ethyl ester

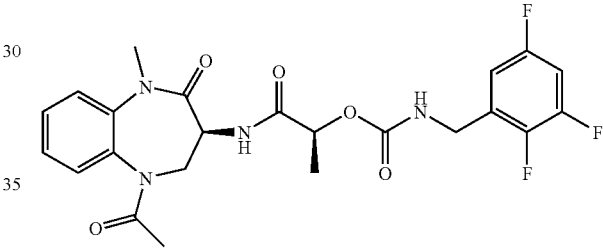

In an analogous manner to that described in Example 57 d), the aminolysis of the carbonic acid (S)-1-((S)-5-acetyl-1-methyl-2-oxo-2,3,4,5-tetrahydro-1H-benzo[b][1,4]diazepin-3-ylcarbamoyl)-ethyl ester 4-nitro-phenyl ester by 2,3,5-trifluoro-benzylamine in dioxane yielded the title compound as a light yellow solid; MS: m/e=510 (M+NH$_4$)$^+$.

EXAMPLE 59

(S)-5-Methyl-4-oxo-3-[(S)-2-(2,2,3,3,3-pentafluoro-propylcarbamoyloxy)-propionylamino]-2,3,4,5-tetrahydro-benzo[b][1,4]diazepine-1-carboxylic acid cyclopropylmethyl ester

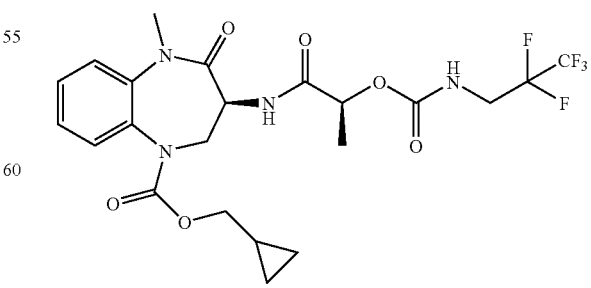

a) (S)-3-tert-Butoxycarbonylamino-5-methyl-4-oxo-2,3,4,5-tetrahydro-benzo[b][1,4]diazepine-1-carboxylic acid cyclopropylmethyl ester A solution of 350 mg (1.2 mmol) of (S)-(1-methyl-2-oxo-2,3,4,5-tetrahydro-1H-benzo[b][1,4]diazepin-3-yl)-carbamic acid tert-butyl ester [Example 56 a)] in 10 ml of N,N-dimethylformamide was treated successively with about 1 g of solid carbon dioxide, 237 mg (1.7 mmol) of bromomethyl-cyclopropane, and 626 mg (1.9 mmol) of cesium carbonate. The reaction mixture was stirred in a sealed flask at 80° C. during the weekend. For the working-up, the solvent was evaporated under reduced pressure and the residue was dissolved in a mixture of 30 ml of ethyl acetate and 10 ml of water. The organic layer was separated, dried over sodium sulphate and evaporated under reduced pressure. For the purification, the crude compound was chromatographed on silica gel using a 3:1-mixture of heptane and ethyl acetate as the eluent. There were obtained 410 mg (87% of theory) of the (S)-3-tert-butoxycarbonylamino-5-methyl-4-oxo-2,3,4,5-tetrahydro-benzo[b][1,4]diazepine-1-carboxylic acid cyclopropylmethyl ester as a white gum; MS: m/e=579 (M+OAc)$^+$.

b) (S)-3-Amino-5-methyl-4-oxo-2,3,4,5-tetrahydro-benzo[b][1,4]diazepine-1-carboxylic acid cyclopropylmethyl ester hydrochloride In an analogous manner to that described in Example 56 c), the cleavage of the tert-butoxy-carbonyl group of the (S)-3-tert-butoxycarbonylamino-5-methyl-4-oxo-2,3,4,5-tetrahydro-benzo[b][1,4]diazepine-1-carboxylic acid cyclopropylmethyl ester yielded the title compound as a light yellow foam.

c) (3S)-((2S)-Hydroxy-propionylamino)-5-methyl-4-oxo-2,3,4,5-tetrahydro-benzo[b][1,4]diazepine-1-carboxylic acid cyclopropylmethyl ester In an analogous manner to that described in Example 53 c), the condensation of (S)-3-amino-5-methyl-4-oxo-2,3,4,5-tetrahydro-benzo[b][1,4]diazepine-1-carboxylic acid cyclopropylmethyl ester hydrochloride with L-(+)-lactic acid yielded the title compound as a light yellow foam; MS: m/e =362 (M+H)$^+$.

d) (S)-5-Methyl-4-oxo-3-[(S)-2-(2,2,3,3,3-pentafluoro-propylcarbamoyloxy)-propionylamino]-2,3,4,5-tetrahydro-benzo[b][1,4]diazepine-1-carboxylic acid cyclopropylmethyl ester In an analogous manner to that described in Example 57 d), the condensation of (3S)-((2S)-hydroxy-propionylamino)-5-methyl-4-oxo-2,3,4,5-tetrahydro-benzo[b][1,4]diazepine-1-carboxylic acid cyclopropylmethyl ester with 4-nitrophenyl chloroformate yielded the (S)-5-methyl-3-[(S)-2-(4-nitro-phenoxycarbonyloxy)-propionylamino]-4-oxo-2,3,4,5-tetrahydro-benzo[b][1,4]diazepine-1-carboxylic acid cyclopropylmethyl ester [MS: m/e=544 (M+NH$_4$)$^+$]. Thereupon, its aminolysis by 2,2,3,3,3-pentafluoro-propylamine yielded the title compound as a white foam; MS: m/e=554 (M+NH$_4$)$^+$.

EXAMPLE 60

(2,2,3,3,3-Pentafluoro-propyl)-carbamic acid (S)-1-[(S)-5-(cyclopropylmethyl-carbamoyl)-2-oxo-1-(2,2,2-trifluoro-ethyl)-2,3,4,5-tetrahydro-1H-benzo[b][1,4]diazepin-3-ylcarbamoyl]-ethyl ester

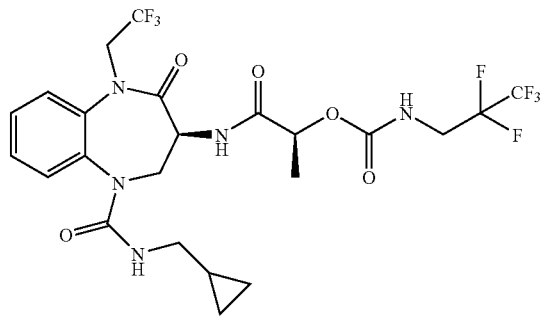

a) [(S)-2-Oxo-1-(2,2,2-trifluoro-ethyl)-2,3,4,5-tetrahydro-1H-benzo[b][1,4]diazepin-3-yl]-carbamic acid tert-butyl ester In an analogous manner to that described in Example 53 a), the alkylation of the (S)-(2-oxo-2,3,4,5-tetrahydro-1H-benzo[b][1,4]diazepin-3-yl)-carbamic acid tert-butyl ester with 2,2,2-trifluoroethyl triflate, yielded, after chromatography on silica gel using a 99:1-mixture of dichloromethane and methanol as the eluent, the title compound as a white foam; MS: m/e=360 (M+H)$^+$.

b) (S)-3-Amino-1-(2,2,2-trifluoro-ethyl)-1,3,4,5-tetrahydro-benzo[b][1,4]diazepin-2-one In an analogous manner to that described in Example 53 b), the cleavage of the tert-butoxy-carbonyl group of the [(S)-2-Oxo-1-(2,2,2-trifluoro-ethyl)-2,3,4,5-tetrahydro-1H-benzo[b][1,4]diazepin-3-yl]-carbamic acid tert-butyl ester yielded the title compound as a light yellow solid; MS: m/e=260 (M+H)$^+$.

c) (3S)-[(2S)-Hydroxy]-N-[2-oxo-1-(2,2,2-trifluoro-ethyl)-2,3,4,5-tetrahydro-1H-benzo[b][1,4]diazepin-3-yl]-propionamide In an analogous manner to that described in Example 53 c), the condensation of (S)-3-amino-1-(2,2,2-trifluoro-ethyl)-1,3,4,5-tetrahydro-benzo[b][1,4]diazepin-2-one with L-(+)-lactic acid yielded the title compound as a yellow solid; MS: m/e=332 (M+H)$^+$.

d) 4-Oxo-(3S)-[(2S)-(2,2,3,3,3-pentafluoro-propylcarbamoyloxy)-propionylamino]-5-(2,2,2-trifluoro-ethyl)-2,3,4,5-tetrahydro-benzo[b][1,4]diazepine-1-carboxylic acid 4-nitro-phenyl ester In an analogous manner to that described in Example 57 d), the reaction of an excess of 4-nitrophenyl chloroformate with (3S)-[(2S)-hydroxy]-N-[2-oxo-1-(2,2,2-trifluoro-ethyl)-2,3,4,5-tetrahydro-1H-benzo[b][1,4]diazepin-3-yl]-propionamide yielded the intermediate (3S)-[(2S)-(4-nitro-phenoxycarbonyloxy)-propionylamino]-4-oxo-5-(2,2,2-trifluoro-ethyl)-2,3,4,5-tetrahydro-benzo[b][1,4]diazepine- 1-carboxylic acid 4-nitro-phenyl ester, which was, thereafter, transformed by treatment with 2,2,3,3,3-pentafluoropropylamine into the title compound and obtained as a white solid; MS: m/e=689 (M+NH$_4$)$^+$.

e) (2,2,3,3,3-Pentafluoro-propyl)-carbamic acid (S)-1-[(S)-5-(cyclopropylmethyl-carbamoyl)-2-oxo-1-(2,2,2-trifluoro-ethyl)-2,3,4,5-tetrahydro-1H-benzo[b][1,4]diazepin-3-ylcarbamoyl]-ethyl ester A solution of 46 mg (0.07 mmol) of 4-oxo-(3S)-[(2S)-(2,2,3,3,3-pentafluoro-propylcarbamoyloxy)-propionylamino]-5-(2,2,2-trifluoro-ethyl)-2,3,4,5-tetrahydro-benzo[b][1,4]diazepine-1-carboxylic acid 4-nitro-phenyl ester in 0.5 ml of dioxane was treated at room temperature with 0.3 ml of aminomethyl-cyclopropane. The mixture was stirred during 2.5 h, then evaporated under reduced pressure. The residue was chromatographed on silica gel using a 98:2-mixture of dichloromethane and methanol as the eluent. There were obtained 6 mg (15% of theory) of the title compound as a white solid; MS: m/e=604 (M+H)$^+$.

EXAMPLE 61

(2,2,3,3,3-Pentafluoro-propyl)-carbamic acid (S)-1-((S)-5-methyl-6-oxo-6,7-dihydro-5H-dibenzo[b,d]azepin-7-ylcarbamoyl)-ethyl ester

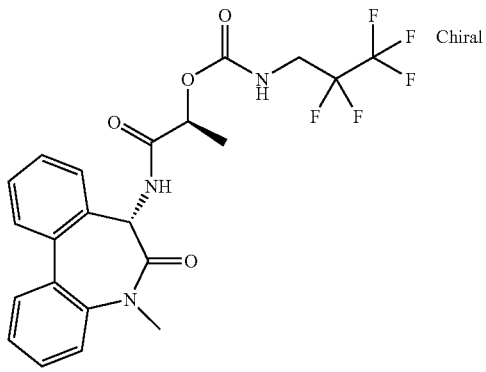

a) (−)-(S)-2-Hydroxy-N—((S)-5-methyl-6-oxo-6,7-dihydro-5H-dibenzo[b,d]azepin-7-yl)-propionamide The title compound, MS: m/e=311.3 (M+H$^+$), was prepared in analogy to example 1a) from (−)-(S)-7-amino-5-methyl-5H,7H-dibenzo[b,d]azepin-6-one hydrochloride and L-(+)-lactic acid.

b) (2,2,3,3,3-Pentafluoro-propyl)-carbamic acid (S)-1-((S)-5-methyl-6-oxo-6,7-dihydro-5H-dibenzo[b,d]azepin-7-ylcarbamoyl)-ethyl ester The title compound, MS: m/e=486.4 (M+H$^+$), was prepared in analogy to example 6 from 2,2,3,3,3-pentafluoropropylamine and (−)-(S)-2-hydroxy-N—((S)-5-methyl-6-oxo-6,7-dihydro-5H-dibenzo[b,d]azepin-7-yl)-propionamide.

EXAMPLE 62

(2,2,3,3,3-Pentafluoro-propyl)-carbamic acid (S)-1-((R)-5-methyl-6-oxo-6,7-dihydro-5H-dibenzo[b,d]azepin-7-ylcarbamoyl)-ethyl ester

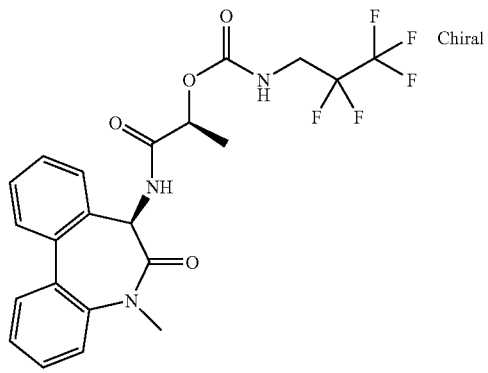

a) (+)-(S)-2-Hydroxy-N—((R)-5-methyl-6-oxo-6,7-dihydro-5H-dibenzo[b,d]azepin-7-yl)-propionamide The title compound, MS: m/e=311.3 (M+H$^+$), was prepared in analogy to example 1a) from (+)-(R)-7-amino-5-methyl-5H,7H-dibenzo[b,d]azepin-6-one hydrochloride and L-(+)-lactic acid.

b) (2,2,3,3,3-Pentafluoro-propyl)-carbamic acid (S)-1-((R)-5-methyl-6-oxo-6,7-dihydro-5H-dibenzo[b,d]azepin-7-ylcarbamoyl)-ethyl ester The title compound, MS: m/e=486.4 (M+H$^+$), was prepared in analogy to example 6 from 2,2,3,3,3-pentafluoropropylamine and (+)-(S)-2-hydroxy-N—((R)-5-methyl-6-oxo-6,7-dihydro-5H-dibenzo[b,d]azepin-7-yl)-propionamide.

EXAMPLE 63

(3,3,3-Trifluoro-propyl)-carbamic acid (S)-1-((S)-5-methyl-6-oxo-6,7-dihydro-5H-dibenzo[b,d]azepin-7-ylcarbamoyl)-ethyl ester

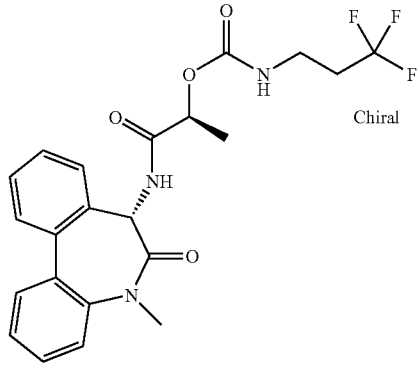

The title compound, MS: m/e=450.4 (M+H$^+$), was prepared in analogy to example 6 from 3,3,3-trifluoropropylamine and (−)-(S)-2-hydroxy-N—((S)-5-methyl-6-oxo-6,7-dihydro-5H-dibenzo[b,d]azepin-7-yl)-propionamide.

EXAMPLE 64

(3,3,4,4,4-Pentafluoro-butyl)-carbamic acid (S)-1-((S)-5-methyl-6-oxo-6,7-dihydro-5H-dibenzo[b,d]azepin-7-ylcarbamoyl)-ethyl ester

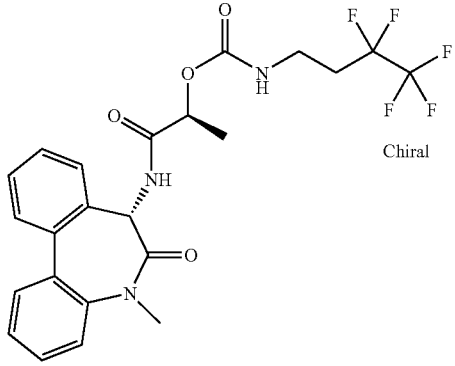

The title compound, MS: m/e=500.4 (M+H⁺), was prepared in analogy to example 6 from 3,3,4,4,4-pentafluorobutylamine and (−)-(S)-2-hydroxy-N—((S)-5-methyl-6-oxo-6,7-dihydro-5H-dibenzo[b,d]azepin-7-yl)-propionamide.

EXAMPLE 65

(2,2,3,3,4,4,4-Heptafluoro-butyl)-carbamic acid (S)-1-((S)-5-methyl-6-oxo-6,7-dihydro-5H-dibenzo[b,d]azepin-7-ylcarbamoyl)-ethyl ester

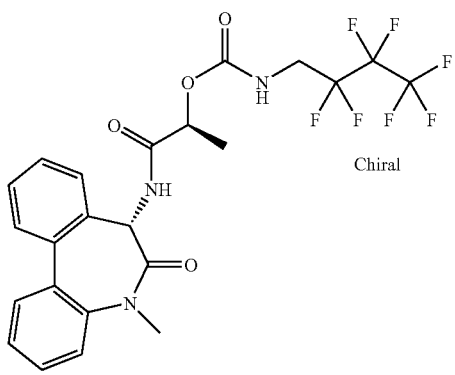

The title compound, MS: m/e=536 (M+H⁺), was prepared in analogy to example 6 from (2,2,3,3,4,4,4-heptafluoro-butyl)-amine and (−)-(S)-2-hydroxy-N—((S)-5-methyl-6-oxo-6,7-dihydro-5H-dibenzo[b,d]azepin-7-yl)-propionamide.

EXAMPLE 66

(3,3,4,4,5,5,6,6,6-Nonafluoro-2-hydroxy-hexyl)-carbamic acid 1-(5-methyl-6-oxo-6,7-dihydro-5H-dibenzo[b,d]azepin-7-ylcarbamoyl)-ethyl ester

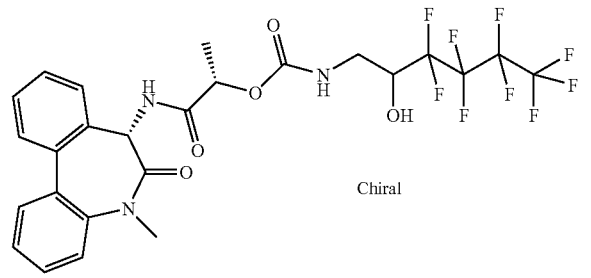

The title compound, MS: m/e=616 (M+H⁺), was prepared in analogy to example 6 from 1-amino-3,3,4,4,5,5,6,6,6-nonafluoro-hexan-2-ol and (−)-(S)-2-hydroxy-N—((S)-5-methyl-6-oxo-6,7-dihydro-5H-dibenzo[b,d]azepin-7-yl)-propionamide.

EXAMPLE 67

(2,2,3,3,4,4,5,5,6,6,7,7,8,8,8-Pentadecafluoro-octyl)-carbamic acid (S)-1-((S)-5-methyl-6-oxo-6,7-dihydro-5H-dibenzo[b,d]azepin-7-ylcarbamoyl)-ethyl ester

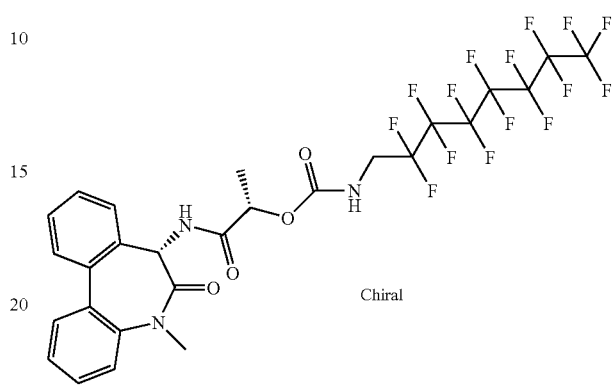

The title compound, MS: m/e=736 (M+H⁺), was prepared in analogy to example 6 from (2,2,3,3,4,4,5,5,6,6,7,7,8,8,8-pentadecafluoro-octyl)-amine and (−)-(S)-2-hydroxy-N—((S)-5-methyl-6-oxo-6,7-dihydro-5H-dibenzo[b,d]azepin-7-yl)-propionamide.

EXAMPLE 68

(2,2,2-Trifluoro-ethyl)-carbamic acid (S)-1-((S)-5-methyl-6-oxo-6,7-dihydro-5H-dibenzo[b,d]azepin-7-ylcarbamoyl)-ethyl ester

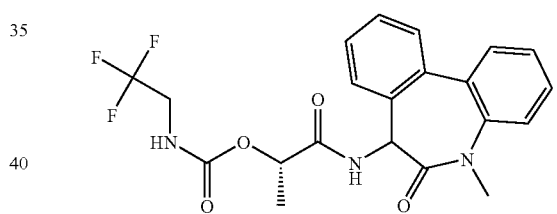

The title compound, MS: m/e=436.5 (M+H⁺), was prepared in analogy to example 6 from 2,2,2-trifluoroethylamine and (−)-(S)-2-hydroxy-N—((S)-5-methyl-6-oxo-6,7-dihydro-5H-dibenzo[b,d]azepin-7-yl)-propionamide.

EXAMPLE 69

(4,4,4-Trifluoro-butyl)-carbamic acid (S)-1-((S)-5-methyl-6-oxo-6,7-dihydro-5H-dibenzo[b,d]azepin-7-ylcarbamoyl)-ethyl ester

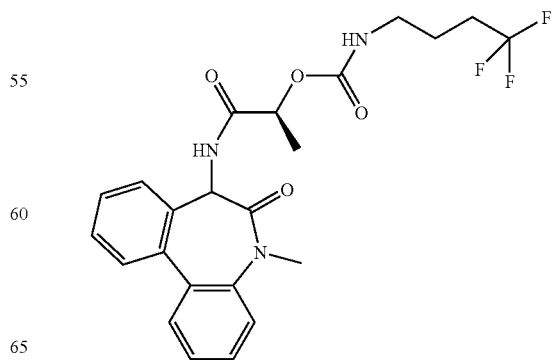

The title compound, MS: m/e=464.5 (M+H⁺), was prepared in analogy to example 6 from 4,4,4-trifluoro-butylamine and (−)-(S)-2-hydroxy-N—((S)-5-methyl-6-oxo-6,7-dihydro-5H-dibenzo[b,d]azepin-7-yl)-propionamide.

EXAMPLE 70

(3,3,4,4-Tetrafluoro-butyl)-carbamic acid (S)-1-((S)-5-methyl-6-oxo-6,7-dihydro-5H-dibenzo[b,d]azepin-7-ylcarbamoyl)-ethyl ester

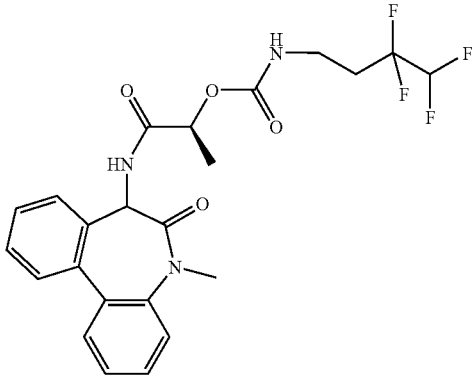

The title compound, MS: m/e=482.6 (M+H⁺), was prepared in analogy to example 6 from 3,3,4,4-tetrafluorobutylamine and (−)-(S)-2-hydroxy-N—((S)-5-methyl-6-oxo-6,7-dihydro-5H-dibenzo[b,d]azepin-7-yl)-propionamide.

EXAMPLE 71

Propyl-carbamic acid (S)-1-((S)-5-methyl-6-oxo-6,7-dihydro-5H-dibenzo[b,d]azepin-7-ylcarbamoyl)-ethyl ester

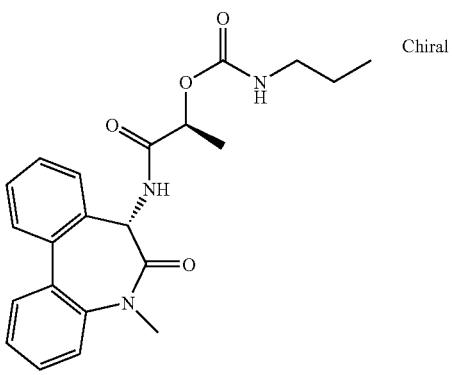

The title compound, MS: m/e=396.4 (M+H⁺), was prepared in analogy to example 6 from Propylamine and (−)-(S)-2-hydroxy-N—((S)-5-methyl-6-oxo-6,7-dihydro-5H-dibenzo[b,d]azepin-7-yl)-propionamide.

EXAMPLE 72

Pentyl-carbamic acid (S)-1-((S)-5-methyl-6-oxo-6,7-dihydro-5H-dibenzo[b,d]azepin-7-ylcarbamoyl)-ethyl ester

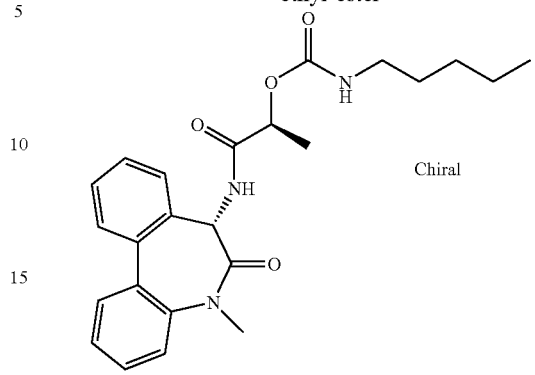

The title compound, MS: m/e=424 (M+H⁺), was prepared in analogy to example 6 from n-pentylamine and (−)-(S)-2-hydroxy-N—((S)-5-methyl-6-oxo-6,7-dihydro-5H-dibenzo[b,d]azepin-7-yl)-propionamide.

EXAMPLE 73

(3,3-Dimethyl-butyl)-carbamic acid (S)-1-((S)-5-methyl-6-oxo-6,7-dihydro-5H-dibenzo[b,d]azepin-7-ylcarbamoyl)-ethyl ester

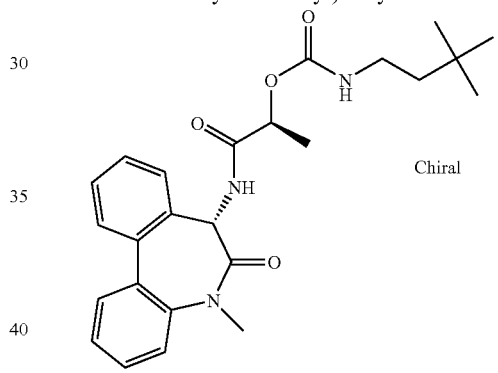

The title compound, MS: m/e=438 (M+H⁺), was prepared in analogy to example 6 from (3,3-dimethyl-butyl)-amine and (−)-(S)-2-hydroxy-N—((S)-5-methyl-6-oxo-6,7-dihydro-5H-dibenzo[b,d]azepin-7-yl)-propionamide.

EXAMPLE 74

((E)-But-2-enyl)-carbamic acid (S)-1-((S)-5-methyl-6-oxo-6,7-dihydro-5H-dibenzo[b,d]azepin-7-ylcarbamoyl)-ethyl ester

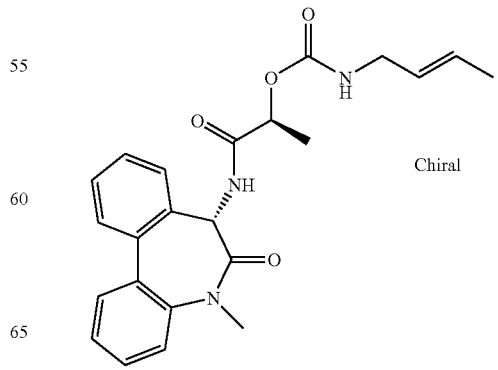

The title compound, MS: m/e=408 (M+H⁺), was prepared in analogy to example 6 from crotylamine and (−)-(S)-2-hydroxy-N—((S)-5-methyl-6-oxo-6,7-dihydro-5H-dibenzo[b,d]azepin-7-yl)-propionamide.

EXAMPLE 75

((E)-3,7-Dimethyl-octa-2,6-dienyl)-carbamic acid (S)-1-((S)-5-methyl-6-oxo-6,7-dihydro-5H-dibenzo[b,d]azepin-7-ylcarbamoyl)-ethyl ester

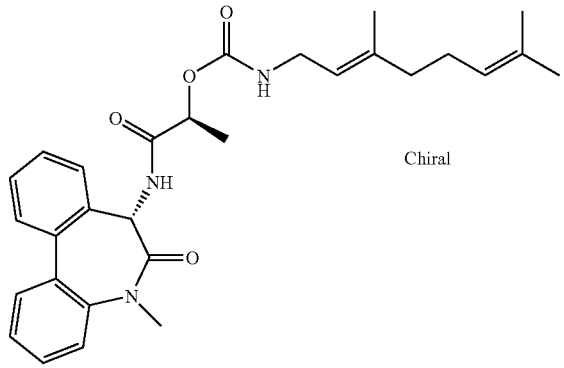

The title compound, MS: m/e=490 (M+H⁺), was prepared in analogy to example 6 from (E)-3,7-dimethyl-octa-2,6-dienylamine and (−)-(S)-2-hydroxy-N—((S)-5-methyl-6-oxo-6,7-dihydro-5H-dibenzo[b,d]azepin-7-yl)-propionamide.

EXAMPLE 76

(2-Methoxy-ethyl)-carbamic acid (S)-1-((S)-5-methyl-6-oxo-6,7-dihydro-5H-dibenzo[b,d]azepin-7-ylcarbamoyl)-ethyl ester

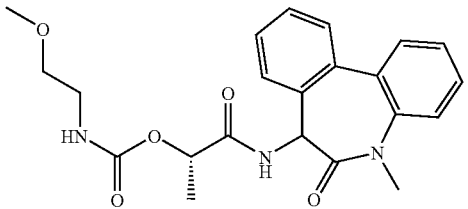

The title compound, MS: m/e=412.5 (M+H⁺), was prepared in analogy to example 6 from 2-methoxyethylamine and (−)-(S)-2-hydroxy-N—((S)-5-methyl-6-oxo-6,7-dihydro-5H-dibenzo[b,d]azepin-7-yl)-propionamide.

EXAMPLE 77

(3-Methoxy-propyl)-carbamic acid (S)-1-((S)-5-methyl-6-oxo-6,7-dihydro-5H-dibenzo[b,d]azepin-7-ylcarbamoyl)-ethyl ester

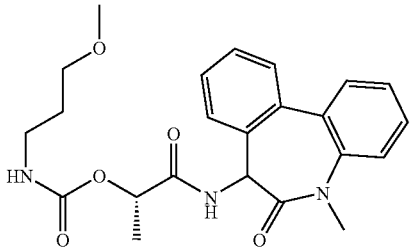

The title compound, MS: m/e=426.5 (M+H⁺), was prepared in analogy to example 6 from 3-methoxypropylamine and (−)-(S)-2-hydroxy-N—((S)-5-methyl-6-oxo-6,7-dihydro-5H-dibenzo[b,d]azepin-7-yl)-propionamide.

EXAMPLE 78

(2-Trimethylsilanyl-ethyl)-carbamic acid (S)-1-((S)-5-methyl-6-oxo-6,7-dihydro-5H-dibenzo[b,d]azepin-7-ylcarbamoyl)-ethyl ester

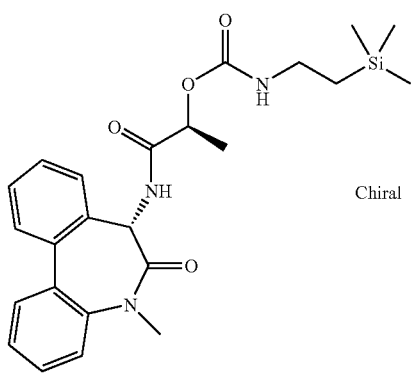

The title compound, MS: m/e=454.5 (M+H⁺), was prepared in analogy to example 6 from 2-trimethylsilanyl-ethylamine and (−)-(S)-2-hydroxy-N-((S)-5-methyl-6-oxo-6,7-dihydro-5H-dibenzo[b,d]azepin-7-yl)-propionamide.

EXAMPLE 79

Phenyl-carbamic acid (S)-1-(5-methyl-6-oxo-6,7-dihydro-5H-dibenzo[b,d]azepin-7-ylcarbamoyl)-ethyl ester The title compound, MS: m/e=430.3 (M+H⁺), was prepared in analogy to example 1 from phenylisocyanate and (S)-2-hydroxy-N-(5-methyl-6-oxo-6,7-dihydro-5H-dibenzo[b,d]azepin-7-yl)-propionamide.

EXAMPLE 80

(2,2,3,3,3-Pentafluoro-propyl)-carbamic acid (S)-1-((S)-6-oxo-6,7-dihydro-5H-dibenzo[b,d]azepin-7-ylcarbamoyl)-ethyl ester

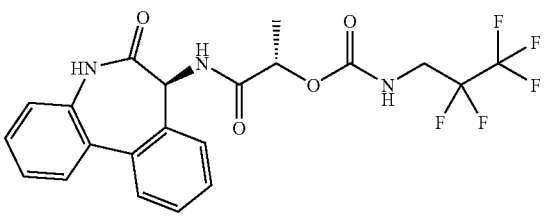

a) 5-(4-Methoxy-benzyl)-5H,7H-dibenzo[b,d]azepin-6-one

To a solution of 0.82 g (4 mmol) of 5H,7H-dibenzo[b,d]azepin-6-one in 15 ml of dimethylformamide at room temperature 0.20 g (5 mmol) of sodium hydride 55% in oil was added. After stirring for 30 min at room temperature 0.75 g (5 mmol) of p-methoxybenzyl chloride were added and stirring was continued at room temperature for 2 hours. For workup the mixture was distributed between water and ethyl acetate. The organic layer was re-extracted with 1 N hydrochloric acid and the aqueous layers were washed with ethyl acetate. The combined organic layers were dried (MgSO4) and concentrated in vacuo. The residue was purified by column chromatography (hexane/ethyl acetate=1:1) to yield 1.175 g (91%) of 5-(4-methoxybenzyl)-5H,7H-dibenzo[b,d]azepin-6-one as a colourless oil; MS: m/e: 330.4 (M+H$^+$).

b) (RS)-7-Amino-5-(4-methoxy-benzyl)-5H,7H-dibenzo[b,d]azepin-6-one

To a solution of 1.15 g (3.5 mmol) 5-(4-methoxybenzyl)-5H,7H-dibenzo[b,d]azepin-6-one in 15 ml of toluene 0.836 g (7 mmol) of isoamyl nitrite were added and the mixture was cooled to 0° C. A solution of 21.4 ml (10.5 mmol) of potassium bis(trimethylsilyl)amide (0.5 M in toluene) was added slowly and stirring was continued for 2 hours at this temperature. Sodium hydrogensulphate solution was added and the mixture was extracted two times with ethylacetate.

The combined organic layers were re-extracted with water and dried (MgSO4). After evaporation of the solvent a solid was obtained, that was purified by column chromatography (dichloromethane/methanol=95:5) to yield 1.03 g (81%) oxime. This compound was dissolved in ethanol (5 ml) and 1.5 ml of 2N hydrochloric acid were added. Palladium on carbon (10%, Degussa 1835, 100 mg) was added and the mixture was hydrogenated at 5 bar H2 pressure for 24 hours at room temperature. The catalyst was filtered off and the solvent was evaporated. The residue was partitioned between dichloromethane (5 ml) and 4N hydrochloric acid (2 ml). The aqueous solution was separated, set to basic pH with sodium hydroxide and extracted 2 times with ethyl acetate. After drying (MgSO$_4$) and evaporation of the ethyl acetate 0.8 g (63%) of the title compound was obtained as a white solid. MS: m/e: 345.3 (M+H$^+$).

c) (S)-7-amino-5-(4-methoxy-benzyl)-5H,7H-dibenzo[b,d]azepin-6-one

Racemic (RS)-7-amino-5-(4-methoxy-benzyl)-5H,7H-dibenzo[b,d]azepin-6-one was separated by chromatography on Chiralpak AD with a 1:3-mixture of isopopanol and heptane as the eluent to yield:
(S)-7-amino-5-(4-methoxy-benzyl)-5H,7H-dibenzo[b,d]azepin-6-one, [α] 589=−146° (1% in CHCl$_3$) and
(R)-7-amino-5-(4-methoxy-benzyl)-5H,7H-dibenzo[b,d]azepin-6-one, [α] 589=+148° (1% in CHCl$_3$).

d) (S)-7-Amino-5H,7H-dibenzo[b,d]azepin-6-one

A solution of 0.55 g (1.6 mmol) (S)-7-amino-5-(4-methoxy-benzyl)-5H,7H-dibenzo[b,d]azepin-6-one, 3.74 ml (50 mmol) trifluoroacetic acid and 1.4 ml (16 mmol) trifluormethane sulfonic acid in 38 ml dichloromethane was stirred at room temperature for 4 hours. The solvent was distilled off and extraction with aqueous sodium bicarbonate solution/ethyl acetate followed by chromatography on silicagel with ethylacetate/methanol (100-95/0-5) yielded 0.35 g (96%) (S)-7-amino-5H,7H-dibenzo[b,d]azepin-6-one as orange solid; MS: m/e: 225.4 (M+H$^+$).

e) (S)-2-Hydroxy-N—((S)-6-oxo-6,7-dihydro-5H-dibenzo[b,d]azepin-7-yl)-propionamide A solution of 0.20 g (0.9 mmol) (S)-7-amino-5H,7H-dibenzo[b,d]azepin-6-one in 8 ml tetrahydrofurane was treated at 0° C. with 0.09 g (0.99 mmol) L-lactic acid, 0.14 g (0.9 mmol) 1-hydroxybenzotriazole hydrate, 314 μl (1.8 mmol) N-ethyldiisopropylamine and 0.18 g (0.9 mmol) N-(3-dimethylaminopropyl)-N'-ethyl-carbodiimid-hydrochlorid. After stirring at room temperature overnight the mixture was extracted with 1N aqueous hydrochloric acid/ ethylacetate. Purification by chromatography on silicagel with ethylacetate/cyclohexane (0-100/100-0) yielded 0.19 g (70%) (S)-2-hydroxy-N—((S)-6-oxo-6,7-dihydro-5H-dibenzo[b,d]azepin-7-yl)-propionamide as white solid; MS: m/e: 297.1 (M+H$^+$).

f) Carbonic acid 4-nitro-phenyl ester (S)-1-((S)-6-oxo-6,7-dihydro-5H-dibenzo[b,d]azepin-7-ylcarbamoyl)-ethyl ester 0.17 g (0.57 mmol) (S)-2-hydroxy-N—((S)-6-oxo-6,7-dihydro-5H-dibenzo[b,d]azepin-7-yl)-propionamide in 5 ml dichloromethane were stirred with 93 μl (1.15 mmol) pyridine and 0.14 g (0.69 mmol) 4-nitrophenyl chloroformate at room temperature overnight. Chromatography on silicagel with ethylacetate/cyclohexane (0-100/100-0) gave 0.27 mg (75%) carbonic acid 4-nitro-phenyl ester (S)-1-((S)-6-oxo-6,7-dihydro-5H-dibenzo[b,d]azepin-7-ylcarbamoyl)-ethyl ester as white solid; MS: m/e: 462.3 (M+H$^+$).

g) (2,2,3,3,3-Pentafluoro-propyl)-carbamic acid (S)-1-((S)-6-oxo-6,7-dihydro-5H-dibenzo[b,d]azepin-7-ylcarbamoyl)-ethyl ester 0.12 g (0.25 mmol) carbonic acid 4-nitro-phenyl ester (S)-1-((S)-6-oxo-6,7-dihydro-5H-dibenzo[b,d]azepin-7-ylcarbamoyl)-ethyl ester and 543 μl 2,2,3,3,3. pentafluoropropylamine were stirred at room temperature over night. Chromatography on silicagel with dichloromethane/ethylacetate (100-0 to 75-25) yielded 0.075 g (63%) (2,2,3,3,3-pentafluoro-propyl)-carbamic acid (S)-1-((S)-6-oxo-6,7-dihydro-5H-dibenzo[b,d]azepin-7-ylcarbamoyl)-ethyl ester as white solid. MS: m/e: 472.1 (M+H$^+$), [α] 589=−76.4° (1% in MeOH).

EXAMPLE 81

(3,3,3-Trifluoro-propyl)-carbamic acid (S)-1-((S)-6-oxo-6,7-dihydro-5H-dibenzo[b,d]azepin-7-ylcarbamoyl)-ethyl ester

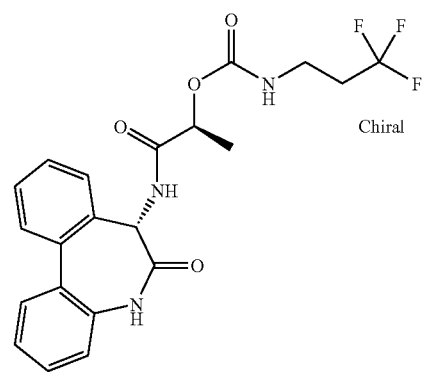

The title compound, MS: m/e=436 (M+H$^+$), was prepared in analogy to example 80 f) and g) from 3,3,3-trifluoropropylamine and (S)-2-hydroxy-N—((S)-6-oxo-6,7-dihydro-5H-dibenzo[b,d]azepin-7-yl)-propionamide.

EXAMPLE 82

(2,2,3,3,3-Pentafluoro-propyl)-carbamic acid (S)-1-((S)-5-cyclopropylmethyl-6-oxo-6,7-dihydro-5H-dibenzo[b,d]azepin-7-ylcarbamoyl)-ethyl ester

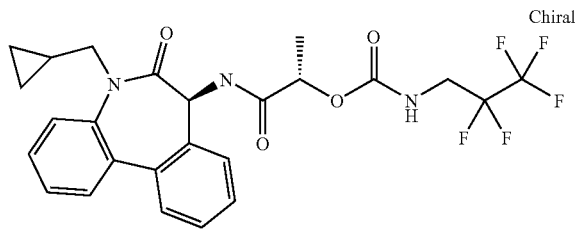

a) (S)-7-Amino-5-cylopropylmethyl-5H,7H-dibenzo[b,d]azepin-6-one (RS)-7-Amino-5-cyclopropylmethyl-5H,7H-dibenzo[b,d]azepin-6-one was separated by HPLC on Chiralpak AD with using a 1:4-mixture of isopropanol and heptane as the eluent to give (S)-7-amino-5-cyclopropylmethyl-5H,7H-dibenzo[b,d]azepin-6-one, [α] 589=−162° (1% in MeOH), and (R)-7-amino-5-cyclopropylmethyl-5H,7H-dibenzo[b,d]azepin-6-one, [α] 589=+163° (1% in MeOH).

b) (S)—N—((S)-5-Cyclopropylmethyl-6-oxo-6,7-dihydro-5H-dibenzo[b,d]azepin-7-yl)-2-hydroxy-propionamide A solution of 0.47 g (1.69 mmol) (S)-7-amino-5-cyclopropylmethyl-5H,7H-dibenzo[b,d]azepin-6-one in 15 ml tetrahydrofurane was treated at 0° C. with 0.17 g (1.86 mmol) L-lactic acid, 0.26 g (1.69 mmol) 1-hydroxybenzotriazole hydrate, 590 µl (3.38 mmol) N-ethyldiisopropylamine and 0.33 g (1.69 mmol) N-(3-dimethylaminopropyl)-N'-ethyl-carbodiimid-hydrochlorid. After stirring at room temperature overnight the mixture was extracted with 1N aqueous hydrochloric acid/ethylacetate. Purification by chromatography on silicagel with ethylacetate/cyclohexane (0-100/100-0) yielded 0.50 g (84%) (S)—N—((S)-5-cyclopropylmethyl-6-oxo-6,7-dihydro-5H-dibenzo[b,d]azepin-7-yl)-2-hydroxy-propionamide as white solid; MS: m/e: 351.4 (M+H$^+$), [α] 589=−131° (1% in MeOH).

c) Carbonic acid (S)-1-((S)-5-cyclopropylmethyl-6-oxo-6,7-dihydro-5H-dibenzo[b,d]azepin-7-ylcarbamoyl)-ethyl ester 4-nitro-phenyl ester 0.46 g (1.32 mmol) (S)—N—((S)-5-cyclopropylmethyl-6-oxo-6,7-dihydro-5H-dibenzo[b,d]azepin-7-yl)-2-hydroxy-propionamide in 15 ml dichloromethane were stirred with 213 µl (2.64 mmol) pyridine and 0.33 g (1.58 mmol) 4-nitrophenyl chloroformate at room temperature overnight. Chromatography on silicagel with ethylacetate/cyclohexane (0-100/100-0) gave 0.63 mg (92%) carbonic acid (S)-1-((S)-5-cyclopropylmethyl-6-oxo-6,7-dihydro-5H-dibenzo[b,d]azepin-7-ylcarbamoyl)-ethyl ester 4-nitro-phenyl ester as a white foam; MS: m/e: 516.5 (M+H$^+$), [α] 589=−164° (0.94% in MeOH).

d) (2,2,3,3,3-Pentafluoro-propyl)-carbamic acid (S)-1-((S)-5-cyclopropylmethyl-6-oxo-6,7-dihydro-5H-dibenzo[b,d]azepin-7-ylcarbamoyl)-ethyl ester 0.61 g (1.18 mmol) carbonic acid (S)-1-((S)-5-cyclopropylmethyl-6-oxo-6,7-dihydro-5H-dibenzo[b,d]azepin-7-ylcarbamoyl)-ethyl ester 4-nitro-phenyl ester and 2.5 ml 2,2,3,3,3. pentafluoropropylamine were stirred at room temperature over night. Chromatography on silicagel with dichloromethane/ethylacetate (100-70/0-30) yielded 0.61 g (98%) (2,2,3,3,3-pentafluoro-propyl)-carbamic acid (S)-1-((S)-5-cyclopropylmethyl-6-oxo-6,7-dihydro-5H-dibenzo[b,d]azepin-7-ylcarbamoyl)-ethyl ester as white solid; MS: m/e: 526.0 (M+H$^+$), [α] 589=−940° (1.1% in MeOH).

EXAMPLE 83

(2,2,3,3,3-Pentafluoro-propyl)-carbamic acid (S)-1-[(S)-6-oxo-5-(2,2,2-trifluoro-ethyl)-6,7-dihydro-5H-dibenzo[b,d]azepin-7-ylcarbamoyl]-ethyl ester

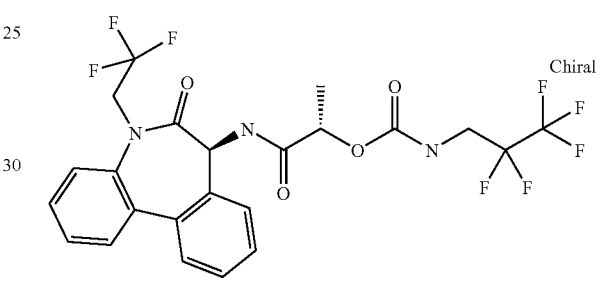

a) 7-Amino-5-(2,2,2-trifluoro-ethyl)-5H,7H-dibenzo[b,d]azepin-6-one

Racemic (RS)-7-amino-5-(2,2,2-trifluoro-ethyl)-5H,7H-dibenzo[b,d]azepin-6-one was separated by chromatography on Chiralpak AD using a 15:85-mixture of isopopanol and heptane as the eluent to yield (S)-7-amino-5-(2,2,2-trifluoro-ethyl)-5H,7H-dibenzo[b,d]azepin-6-one, [α] 589=−290 (1% in CHCl$_3$) and (R)-7-amino-5-(2,2,2-trifluoro-ethyl)-5H,7H-dibenzo[b,d]azepin-6-one, [α] 589=+260 (1% in CHCl$_3$).

b) (S)-2-Hydroxy-N—[(S)-6-oxo-5-(2,2,2-trifluoro-ethyl)-6,7-dihydro-5H-dibenzo[b,d]azepin-7-yl]-propionamide A solution of 0.26 g (0.85 mmol) (S)-7-amino-5-(2,2,2-trifluoro-ethyl)-5H,7H-dibenzo[b,d]azepin-6-one in 18 ml tetrahydrofurane was treated at 0° C. with 0.08 g (0.94 mmol) L-lactic acid, 0.13 g (0.85 mmol) 1-hydroxybenzotriazole hydrate, 297 µl (1.70 mmol) N-ethyldiisopropylamine and 0.17 g (0.85 mmol) N-(3-dimethylaminopropyl)-N'-ethyl-carbodiimid-hydrochlorid. After stirring at room temperature overnight the mixture was extracted with 1N aqueous hydrochloric acid/ethylacetate. Purification by chromatography on silicagel with ethylacetate/heptane (0-100/100-0) yielded 0.22 g (68%) (S)-2-hydroxy-N—[(S)-6-oxo-5-(2,2,2-trifluoro-ethyl)-6,7-dihydro-5H-dibenzo[b,d]azepin-7-yl]-propionamide as grey solid, MS: m/e: 379.4 (M+H$^+$), [α] 589=−23° (1.1% in CHCl$_3$).

c) Carbonic acid 4-nitro-phenyl ester (S)-1-[(S)-6-oxo-5-(2,2,2-trifluoro-ethyl)-6,7-dihydro-5H-dibenzo[b,d]azepin-7-ylcarbamoyl]-ethyl ester 0.20 g (0.53 mmol(S)-2-hydroxy-N-[(S)-6-oxo-5-(2,2,2-trifluoro-ethyl)-6,7-dihydro-5H-dibenzo[b,d]azepin-7-yl]-propionamide in 5 ml dichloromethane were stirred with 85 µl (1.06 mmol) pyridine and 0.13 g (0.64 mmol) 4-nitro-phenyl chloroformate at room temperature overnight. Chromatography on silicagel with ethylacetate/cyclohexane (0-100/100-0) gave 0.07 mg (23%) carbonic acid 4-nitro-phenyl ester (S)-1-[(S)-6-oxo-5-(2,2,2-trifluoro-ethyl)-6,7-dihydro-5H-dibenzo[b,d]azepin-7-ylcarbamoyl]-ethyl ester as white solid, MS: m/e: 544.3 (M+H$^+$).

d) (2,2,3,3,3-Pentafluoro-propyl)-carbamic acid (S)-1-[(S)-6-oxo-5-(2,2,2-trifluoro-ethyl)-6,7-dihydro-5H-dibenzo[b,d]azepin-7-ylcarbamoyl]-ethyl ester 0.065 g (0.12 mmol) carbonic acid 4-nitro-phenyl ester (S)-1-[(S)-6-oxo-5-(2,2,2-trifluoro-ethyl)-6,7-dihydro-5H-dibenzo[b,d]azepin-7-ylcarbamoyl]-ethyl ester and 0.26 ml 2,2,3,3,3. pentafluoropropylamine were stirred at room temperature over night. Chromatography on silicagel with dichloromethane/ethylacetate (100-40/0-60) yielded 0.06 g (86%) (2,2,3,3,3-Pentafluoro-propyl)-carbamic acid (S)-1-[(S)-6-oxo-5-(2,2,2-trifluoro-ethyl)-6,7-dihydro-5H-dibenzo[b,d]azepin-7-ylcarbamoyl]-ethyl ester as white foam, MS: m/e: 554.3 (M+H$^+$), [α] 589=−4.40° (0.75% in CHCl$_3$).

What is claimed is:

1. A compound of formula

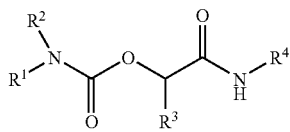

I wherein
- $R^1$ is —(CHR')$_q$-aryl or —(CHR')$_q$-heteroaryl, which is unsubstituted or mono, di- or tri-substituted by lower alkyl, lower alkoxy, CF$_3$ or halogen,
  wherein heteroaryl is selected from the group consisting of pyridyl, pyrazinyl, pyrimidinyl, triazinyl, thiazolyl, thiophenyl, furyl, pyrazol, pyrrolyl, and imidzaolyl;
  or is
  lower alkyl, lower alkenyl, —(CH$_2$)$_n$—Si(CH$_3$)$_3$, —(CH$_2$)$_n$—O-lower alkyl, —(CH$_2$)$_n$—S-lower alkyl, —(CH$_2$)$_q$-cycloalkyl, or —(CH$_2$)$_n$—[CH(OH)]$_m$—(CF$_2$)$_p$—CH$_q$F$_{(3-q)}$,
  or is
  —(CH$_2$)$_n$—CR$_2$—CF$_3$, wherein the two R radicals form together with the carbon atom a cycloalkyl ring;
- R' is hydrogen or lower alkyl;
- n is 1, 2 or 3;
- m is 0 or 1;
- p is 0, 1, 2, 3, 4, 5 or 6;
- q is 0, 1, 2 or 3;
- $R^2$ is hydrogen or lower alkyl;
- $R^3$ is hydrogen, lower alkyl, —CH$_2$CF$_2$CF$_3$, CH$_2$CF$_3$, (CH$_2$)$_2$CF$_3$, CF$_3$, CHF$_2$, CH$_2$F or is aryl optionally mono, di or tri-substituted by halogen,
  or is —(CH$_2$)$_n$NR$^5$R$^6$ wherein R$^5$ and R$^6$ are each independently selected from hydrogen or lower alkyl;

$R^4$ is one of the following groups

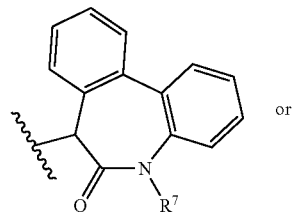
a)

or

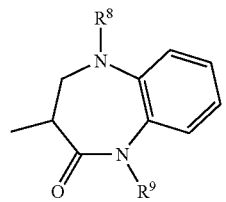
b)

wherein
- $R^7$ is hydrogen, lower alkyl, —(CH$_2$)$_n$—CF$_3$ or —(CH$_2$)$_n$-cycloalkyl;
- $R^8$ is hydrogen, lower alkyl, —C(O)-phenyl, —C(O)-lower alkyl, —C(O)O—(CH$_2$)$_n$-cycloalkyl, —C(O)O—(CH$_2$)$_n$-lower alkyl, —C(O)NH—(CH$_2$)$_n$-lower alkyl or —C(O)NH—(CH$_2$)$_n$-cycloalkyl;
- $R^9$ is hydrogen, lower alkyl, —(CH$_2$)$_n$-cycloalkyl or —(CH$_2$)$_n$—CF$_3$;

or a pharmaceutically acceptable salt, optically pure enantiomer, racemate or diastereomeric mixture thereof.

2. A compound of formula

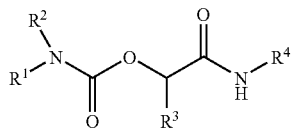

I-1 wherein
- $R^1$ is —(CH$_2$)$_n$-aryl or —(CH$_2$)$_n$-heteroaryl, which is unsubstituted or mono, di- or tri-substituted by lower alkyl, lower alkoxy, CF$_3$ or halogen,
  wherein heteroaryl is selected from the group consisting of pyridyl, pyrazinyl, pyrimidinyl, triazinyl, thiazolyl, thiophenyl, furyl, pyrazol, pyrrolyl, and imidzaolyl;
  or is
  lower alkyl, —(CH$_2$)$_n$—O-lower alkyl, —(CH$_2$)$_n$—S-lower alkyl, —(CH$_2$)$_n$-cycloalkyl, —(CH$_2$)$_n$—CH$_2$F, —(CH$_2$)$_n$—CF$_3$, or —(CH$_2$)$_n$—CF$_2$—CF$_3$, —(CH$_2$)$_n$—CF$_2$—CHF$_2$,
  or is
  —(CH$_2$)$_n$—CR$_2$—CF$_3$, wherein the two R radicals form together with the carbon atom a cycloalkyl ring;
- $R^2$ is hydrogen or lower alkyl;
- $R^3$ is hydrogen, lower alkyl, —CH$_2$F, CHF$_2$, CF$_3$, aryl optionally mono, di or tri-substituted by halogen, or —(CH$_2$)$_n$NR$^5$R$^6$ wherein R$^5$ and R$^6$ are each independently selected from hydrogen or lower alkyl;

R⁴ is one of the following groups

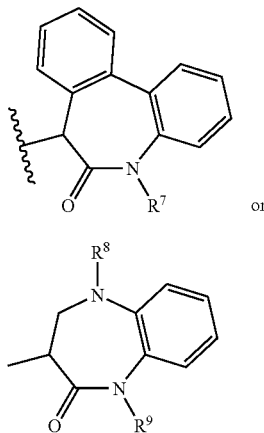

a)

b)

wherein
R⁷ is lower alkyl or —(CH₂)₂-cycloalkyl;
R⁸, R⁹ are each independently selected from hydrogen, lower alkyl, —(CH₂)ₙ-cycloalkyl or —C(O)-phenyl;
or a pharmaceutically acceptable salt, optically pure enantiomer, racemate or diastereomeric mixture thereof.

3. A compound of formula I in accordance with claim 1, wherein R⁴ is a).

4. A compound of formula I in accordance with claim 3, wherein R¹ is —CH₂-phenyl, unsubstituted or mono, di- or tri-substituted by lower alkyl, lower alkoxy, CF₃ or halogen.

5. A compound of formula I in accordance with claim 4, wherein the compound is selected from
(2,3-difluoro-benzyl)-carbamic acid (S)-1-(5-methyl-6-oxo-6,7-dihydro-5H-dibenzo[b,d]azepin-7-ylcarbamoyl)-ethyl ester,
(2-trifluoromethyl-benzyl)-carbamic acid (S)-1-(5-methyl-6-oxo-6,7-dihydro-5H-dibenzo[b,d]azepin-7-ylcarbamoyl)-ethyl ester,
(2-methyl-benzyl)-carbamic acid (S)-1-(5-methyl-6-oxo-6,7-dihydro-5H-dibenzo[b,d]azepin-7-ylcarbamoyl)-ethyl ester
(2,4-difluoro-benzyl)-carbamic acid (S)-1-(5-methyl-6-oxo-6,7-dihydro-5H-dibenzo[b,d]azepin-7-ylcarbamoyl)-ethyl ester,
(3,4-difluoro-benzyl)-carbamic acid (S)-1-(5-methyl-6-oxo-6,7-dihydro-5H-dibenzo[b,d]azepin-7-ylcarbamoyl)-ethyl ester,
(2,3,5-trifluoro-benzyl)-carbamic acid (S)-1-(5-methyl-6-oxo-6,7-dihydro-5H-dibenzo[b,d]azepin-7-ylcarbamoyl)-ethyl ester and
(2,3,6-trifluoro-benzyl)-carbamic acid (S)-1-(5-methyl-6-oxo-6,7-dihydro-5H-dibenzo[b,d]azepin-7-ylcarbamoyl)-ethyl ester.

6. A compound of formula I in accordance with claim 3, wherein R¹ is
—(CH₂)ₙ—[CH(OH)]ₘ—(CF₂)ₚ—CH$_q$F$_{(3-q)}$.

7. A compound of formula I in accordance with claim 6, which compound is selected from
(2,2,2-trifluoro-ethyl)-carbamic acid (S)-1-(5-methyl-6-oxo-6,7-dihydro-5H-dibenzo[b,d]azepin-7-ylcarbamoyl)-ethyl ester,
(2,2,3,3,3-pentafluoro-propyl)-carbamic acid (S)-1-(5-methyl-6-oxo-6,7-dihydro-5H-dibenzo[b,d]azepin-7-ylcarbamoyl)-ethyl ester,
(2,2,3,3,3-pentafluoro-propyl)-carbamic acid 2-fluoro-1-(5-methyl-6-oxo-6,7-dihydro-5H-dibenzo[b,d]azepin-7-ylcarbamoyl)-ethyl ester,
(2,2,3,3,3-pentafluoro-propyl)-carbamic acid 1-(5-methyl-6-oxo-6,7-dihydro-5H-dibenzo[b,d]azepin-7-ylcarbamoyl)-propyl ester,
(2,2,2-trifluoro-ethyl)-carbamic acid 1-(5-methyl-6-oxo-6,7-dihydro-5H-dibenzo[b,d]azepin-7-ylcarbamoyl)-propyl ester,
(2,2,2-trifluoro-ethyl)-carbamic acid 2-fluoro-1-(5-methyl-6-oxo-6,7-dihydro-5H-dibenzo[b,d]azepin-7-ylcarbamoyl)-ethyl ester,
(2,2,3,3,3-pentafluoro-propyl)-carbamic acid (S)-1-((S)-5-methyl-6-oxo-6,7-dihydro-5H-dibenzo[b,d]azepin-7-ylcarbamoyl)-ethyl ester,
(3,3,3-trifluoro-propyl)-carbamic acid (S)-1-((S)-5-methyl-6-oxo-6,7-dihydro-5H-dibenzo[b,d]azepin-7-ylcarbamoyl)-ethyl ester,
(3,3,4,4,4-pentafluoro-butyl)-carbamic acid (S)-1-((S)-5-methyl-6-oxo-6,7-dihydro-5H-dibenzo[b,d]azepin-7-ylcarbamoyl)-ethyl ester,
(2,2,3,3,4,4,4-heptafluoro-butyl)-carbamic acid (S)-1-((S)-5-methyl-6-oxo-6,7-dihydro-5H-dibenzo[b,d]azepin-7-ylcarbamoyl)-ethyl ester,
(2,2,3,3,4,4,5,5,6,6,7,7,8,8,8-pentadecafluoro-octyl)-carbamic acid (S)-1-((S)-5-methyl-6-oxo-6,7-dihydro-5H-dibenzo[b,d]azepin-7-ylcarbamoyl)-ethyl ester,
(2,2,2-trifluoro-ethyl)-carbamic acid (S)-1-((S)-5-methyl-6-oxo-6,7-dihydro-5H-dibenzo[b,d]azepin-7-ylcarbamoyl)-ethyl ester,
(2,2,3,3,3-pentafluoro-propyl)-carbamic acid (S)-1-((S)-6-oxo-6,7-dihydro-5H-dibenzo[b,d]azepin-7-ylcarbamoyl)-ethyl ester,
(3,3,3-trifluoro-propyl)-carbamic acid (S)-1-((S)-6-oxo-6,7-dihydro-5H-dibenzo[b,d]azepin-7-ylcarbamoyl)-ethyl ester,
(2,2,3,3,3-pentafluoro-propyl)-carbamic acid (S)-1-((S)-5-cyclopropylmethyl-6-oxo-6,7-dihydro-5H-dibenzo[b,d]azepin-7-ylcarbamoyl)-ethyl ester and
(2,2,3,3,3-pentafluoro-propyl)-carbamic acid (S)-1-[(S)-6-oxo-5-(2,2,2-trifluoro-ethyl)-6,7-dihydro-5H-dibenzo[b,d]azepin-7-ylcarbamoyl]-ethyl ester.

8. A compound of formula I in accordance with claim 3, wherein R¹ is —(CH₂)ₙ-cycloalkyl.

9. A compound of formula I in accordance with claim 8, wherein the compound is cyclopropylmethyl-carbamic acid 3-methyl-1-(5-methyl-6-oxo-6,7-dihydro-5H-dibenzo[b,d]azepin-7-ylcarbamoyl)-butyl ester.

10. A compound of formula I in accordance with claim 3, wherein R¹ is —(CH₂)ₙ—CR₂—CF₃, wherein the two R radicals form together with the carbon atom a cycloalkyl ring.

11. A compound of formula I in accordance with claim 10, wherein the compound is
(1-trifluoromethyl-cyclopropylmethyl)-carbamic acid (S)-1-(5-methyl-6-oxo-6,7-dihydro-5H-dibenzo[b,d]azepin-7-ylcarbamoyl)-ethyl ester.

12. A compound of formula I in accordance with claim 3, wherein R¹ is lower alkyl.

13. A compound of formula I in accordance with claim 12, wherein the compound is (3,3-dimethyl-butyl)-carbamic acid (S)-1-((S)-5-methyl-6-oxo-6,7-dihydro-5H-dibenzo[b,d]azepin-7-ylcarbamoyl)-ethyl ester.

14. A compound of formula I in accordance with claim 1, wherein R⁴ is b).

15. A compound of formula I in accordance with claim 14, wherein the compound is selected from (2,2,3,3,3-pentafluoro-propyl)-carbamic acid (S)-1-((S)-5-benzoyl-1-methyl-2-oxo-2,3,4,5-tetrahydro-1H-benzo[b][1,4]diazepin-3-ylcarbamoyl)-ethyl ester (2,2,3,3,3-pentafluoro-propyl)-carbamic acid (S)-1-((S)-5-acetyl-1-methyl-2-oxo-2,3,4,5-tetrahydro-1H-benzo[b][1,4]diazepin-3-ylcarbamoyl)-ethyl ester (S)-5-methyl-4-oxo-3-[(S)-2-(2,2,3,3,3-pentafluoro-propylcarbamoyloxy)-propionylamino]-2,3,4,5-tetrahydro-benzo[b][1,4]diazepine-1-carboxylic acid cyclopropylmethyl ester and (2,2,3,3,3-pentafluoro-propyl)-carbamic acid (S)-1-[(S)-5-(cyclopropylmethyl-carbamoyl)-2-oxo-1-(2,2,2-trifluoro-ethyl)-2,3,4,5-tetrahydro-1H-benzo[b][1,4]diazepin-3-ylcarbamoyl]-ethyl ester.

16. A compound of according to claim 1, selected from

Benzyl-carbamic acid (S)-1-(5-methyl-6-oxo-6,7-dihydro-5H-dibenzo[b,d]azepin-7-ylcarbamoyl)-ethyl ester, Tolyl-carbamic acid (S)-1-(5-methyl-6-oxo-6,7-dihydro-5H-dibenzo[b,d]azepin-7-ylcarbamoyl)-ethyl ester, (4-Fluoro-phenyl)-carbamic acid (S)-1-(5-methyl-6-oxo-6,7-dihydro-5H-dibenzo[b,d]azepin-7-ylcarbamoyl)-ethyl ester, (3-Fluoro-phenyl)-carbamic acid (S)-1-(5-methyl-6-oxo-6,7-dihydro-5H-dibenzo[b,d]azepin-7-ylcarbamoyl)-ethyl ester, Thiophen-2-yl-carbamic acid (S)-1-(5-methyl-6-oxo-6,7-dihydro-5H-dibenzo[b,d]azepin-7-ylcarbamoyl)-ethyl ester, Ethyl-carbamic acid (S)-1-(5-methyl-6-oxo-6,7-dihydro-5H-dibenzo[b,d]azepin-7-ylcarbamoyl)-ethyl ester, (2-Methoxy-ethyl)-carbamic acid (S)-1-(5-methyl-6-oxo-6,7-dihydro-5H-dibenzo[b,d]azepin-7-ylcarbamoyl)-ethyl ester, Propyl-carbamic acid (S)-1-(5-methyl-6-oxo-6,7-dihydro-5H-dibenzo[b,d]azepin-7-ylcarbamoyl)-ethyl ester, Cyclopropylmethyl-carbamic acid (S)-1-(5-methyl-6-oxo-6,7-dihydro-5H-dibenzo[b,d]azepin-7-ylcarbamoyl)-ethyl ester, and (2-Methylsulfanyl-ethyl)-carbamic acid (S)-1-(5-methyl-6-oxo-6,7-dihydro-5H-dibenzo[b,d]azepin-7-ylcarbamoyl)-ethyl ester.

17. A compound of according to claim 1, selected from (3-Methoxy-propyl)-carbamic acid (S)-1-(5-methyl-6-oxo-6,7-dihydro-5H-dibenzo[b,d]azepin-7-ylcarbamoyl)-ethyl ester, Cyclopropyl-carbamic acid (S)-1-(5-methyl-6-oxo-6,7-dihydro-5H-dibenzo[b,d]azepin-7-ylcarbamoyl)-ethyl ester, Isopropyl-carbamic acid (S)-1-(5-methyl-6-oxo-6,7-dihydro-5H-dibenzo[b,d]azepin-7-ylcarbamoyl)-ethyl ester, (2-Fluoro-ethyl)-carbamic acid (S)-1-(5-methyl-6-oxo-6,7-dihydro-5H-dibenzo[b,d]azepin-7-ylcarbamoyl)-ethyl ester, (4-Fluoro-benzyl)-carbamic acid (S)-1-(5-methyl-6-oxo-6,7-dihydro-5H-dibenzo[b,d]azepin-7-ylcarbamoyl)-ethyl ester, (2-Fluoro-benzyl)-carbamic acid (S)-1-(5-methyl-6-oxo-6,7-dihydro-5H-dibenzo[b,d]azepin-7-ylcarbamoyl)-ethyl ester, (2,5-Difluoro-benzyl)-carbamic acid (S)-1-(5-methyl-6-oxo-6,7-dihydro-5H-dibenzo[b,d]azepin-7-ylcarbamoyl)-ethyl ester,

[2-(3-Fluoro-phenyl)-ethyl]-carbamic acid (S)-1-(5-methyl-6-oxo-6,7-dihydro-5H-dibenzo[b,d]azepin-7-ylcarbamoyl)-ethyl ester, and (3,5-Difluoro-benzyl)-carbamic acid (S)-1-(5-methyl-6-oxo-6,7-dihydro-5H-dibenzo[b,d]azepin-7-ylcarbamoyl)-ethyl ester.

18. A compound of according to claim 1, selected from (2-Chloro-benzyl)-carbamic acid (S)-1-(5-methyl-6-oxo-6,7-dihydro-5H-dibenzo[b,d]azepin-7-ylcarbamoyl)-ethyl ester, (2-Methoxy-benzyl)-carbamic acid (S)-1-(5-methyl-6-oxo-6,7-dihydro-5H-dibenzo[b,d]azepin-7-ylcarbamoyl)-ethyl ester, (2,4-Difluoro-benzyl)-carbamic acid (S)-1-(5-methyl-6-oxo-6,7-dihydro-5H-dibenzo[b,d]azepin-7-ylcarbamoyl)-ethyl ester, (3,4-Difluoro-benzyl)-carbamic acid (S)-1-(5-methyl-6-oxo-6,7-dihydro-5H-dibenzo[b,d]azepin-7-ylcarbamoyl)-ethyl ester, (2-Fluoro-5-trifluoromethyl-benzyl)-carbamic acid (S)-1-(5-methyl-6-oxo-6,7-dihydro-5H-dibenzo[b,d]azepin-7-ylcarbamoyl)-ethyl ester, (2,6-Difluoro-benzyl)-carbamic acid (S)-1-(5-methyl-6-oxo-6,7-dihydro-5H-dibenzo[b,d]azepin-7-ylcarbamoyl)-ethyl ester, ((R)-1-Phenyl-ethyl)-carbamic acid (S)-1-(5-methyl-6-oxo-6,7-dihydro-5H-dibenzo[b,d]azepin-7-ylcarbamoyl)-ethyl ester, ((S)-1-Phenyl-ethyl)-carbamic acid (S)-1-(5-methyl-6-oxo-6,7-dihydro-5H-dibenzo[b,d]azepin-7-ylcarbamoyl)-ethyl ester, and Benzyl-methyl-carbamic acid (S)-1-(5-methyl-6-oxo-6,7-dihydro-5H-dibenzo[b,d]azepin-7-ylcarbamoyl)-ethyl ester.

19. A compound of according to claim 1, selected from (2,2,3,3,3-Pentafluoro-propyl)-carbamic acid (R)-1-(5-methyl-6-oxo-6,7-dihydro-5H-dibenzo[b,d]azepin-7-ylcarbamoyl)-ethyl ester, (2,2,3,3,3-Pentafluoro-propyl)-carbamic acid 3-methyl-(S)-1-(5-methyl-6-oxo-6,7-dihydro-5H-dibenzo[b,d]azepin-7-ylcarbamoyl)-butyl ester, Benzyl-carbamic acid 3-methyl-(S)-1-(5-methyl-6-oxo-6,7-dihydro-5H-dibenzo[b,d]azepin-7-ylcarbamoyl)-butyl ester, (2,2,3,3,3-Pentafluoro-propyl)-carbamic acid 2-dimethylamino-1-(5-methyl-6-oxo-6,7-dihydro-5H-dibenzo[b,d]azepin-7-ylcarbamoyl)-ethyl ester, Cyclopropylmethyl-carbamic acid (5-methyl-6-oxo-6,7-dihydro-5H-dibenzo[b,d]azepin-7-ylcarbamoyl)-methyl ester, Cyclopropylmethyl-carbamic acid (3,5-difluoro-phenyl)-(5-methyl-6-oxo-6,7-dihydro-5H-dibenzo[b,d]azepin-7-ylcarbamoyl)-methyl ester, (4,4,4-Trifluoro-butyl)-carbamic acid (S)-1-(5-methyl-6-oxo-6,7-dihydro-5H-dibenzo[b,d]azepin-7-ylcarbamoyl)-ethyl ester, (3,3,4,4-Tetrafluoro-butyl)-carbamic acid (S)-1-(5-methyl-6-oxo-6,7-dihydro-5H-dibenzo[b,d]azepin-7-ylcarbamoyl)-ethyl ester, and (3,3,4,4-Tetrafluoro-butyl)-carbamic acid 1-(5-methyl-6-oxo-6,7-dihydro-5H-dibenzo[b,d]azepin-7-ylcarbamoyl)-propyl ester.

20. A compound of according to claim 1, selected from (3,3,4,4-Tetrafluoro-butyl)-carbamic acid 2-fluoro-1-(5-methyl-6-oxo-6,7-dihydro-5H-dibenzo[b,d]azepin-7-ylcarbamoyl)-ethyl ester, Trifluoromethyl-cyclopropylmethyl)-carbamic acid 2-fluoro-1-(5-methyl-6-oxo-6,7-dihydro-5H-dibenzo[b,d]azepin-7-ylcarbamoyl)-ethyl ester, (2,2,3,3,3-Pentafluoro-propyl)-carbamic acid (S)-1-((S)-1-cyclopropylmethyl-5-methyl-2-oxo-2,3,4,5-tetrahydro-1H-benzo[b][1,4]diazepin-3-ylcarbamoyl)-ethyl ester, (2,2,2-Trifluoro-ethyl)-carbamic acid (S)-1-((S)-1-cyclopropylmethyl-5-methyl-2-oxo-2,3,4,5-tetrahydro-1H-benzo[b][1,4]diazepin-3-ylcarbamoyl)-ethyl ester, Trifluoromethyl-cyclopropylmethyl)-carbamic acid (S)-1-((S)-1-cyclopropylmethyl-5-methyl-2-oxo-2,3,4,5-tetrahydro-1H-benzo[b][1,4]diazepin-3-ylcarbamoyl)-ethyl ester, (2,3,5-Trifluoro-benzyl)-carbamic acid (S)-1-((S)-5-acetyl-1-methyl-2-oxo-2,3,4,5-tetrahydro-1H-benzo[b][1,4]diazepin-3-ylcarbamoyl)-ethyl ester, (2,2,3,3,3-Pentafluoro-propyl)-carbamic acid (S)-1-((R)-5-methyl-6-oxo-6,7-dihydro-5H-dibenzo[b,d]azepin-7-ylcarbamoyl)-ethyl ester, (3,3,4,4,5,5,6,6,6-Nonafluoro-2-hydroxy-hexyl)-carbamic acid 1-(5-methyl-6-oxo-6,7-dihydro-5H-dibenzo[b,d]azepin-7-ylcarbamoyl)-ethyl ester, and (4,4,4-Trifluoro-butyl)-carbamic acid (S)-1-((S)-5-methyl-6-oxo-6,7-dihydro-5H-dibenzo[b,d]azepin-7-ylcarbamoyl)-ethyl ester.

21. A compound of according to claim 1, selected from (3,3,4,4-Tetrafluoro-butyl)-carbamic acid (S)-1-((S)-5-methyl-6-oxo-6,7-dihydro-5H-dibenzo[b,d]azepin-7-ylcarbamoyl)-ethyl ester, Propyl-carbamic acid (S)-1-((S)-5-methyl-6-oxo-6,7-dihydro-5H-dibenzo[b,d]azepin-7-ylcarbamoyl)-ethyl ester, Pentyl-carbamic acid (S)-1-((S)-5-methyl-6-oxo-6,7-dihydro-5H-dibenzo[b,d]azepin-7-ylcarbamoyl)-ethyl ester, ((E)-But-2-enyl)-carbamic acid (S)-1-((S)-5-methyl-6-oxo-6,7-dihydro-5H-dibenzo[b,d]azepin-7-ylcarbamoyl)-ethyl ester, ((E)-3,7-Dimethyl-octa-2,6-dienyl)-carbamic acid (S)-1-((S)-5-methyl-6-oxo-6,7-dihydro-5H-dibenzo[b,d]azepin-7-ylcarbamoyl)-ethyl ester, (2-Methoxy-ethyl)-carbamic acid (S)-1-((S)-5-methyl-6-oxo-6,7-dihydro-5H-dibenzo[b,d]azepin-7-ylcarbamoyl)-ethyl ester, (3-Methoxy-propyl)-carbamic acid (S)-1-((S)-5-methyl-6-oxo-6,7-dihydro-5H-dibenzo[b,d]azepin-7-ylcarbamoyl)-ethyl ester, (2-Trimethylsilanyl-ethyl)-carbamic acid (S)-1-((S)-5-methyl-6-oxo-6,7-dihydro-5H-dibenzo[b,d]azepin-7-ylcarbamoyl)-ethyl ester, and Phenyl-carbamic acid (S)-1-(5-methyl-6-oxo-6,7-dihydro-5H-dibenzo[b,d]azepin-7-ylcarbamoyl)-ethyl ester.

22. A composition comprising a compound of formula

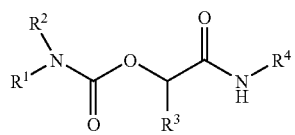

I wherein $R^1$ is —(CHR')$_q$-aryl or —(CHR')$_q$-heteroaryl, which is unsubstituted or mono, di- or tri-substituted by lower alkyl, lower alkoxy, $CF_3$ or halogen, wherein heteroaryl is selected from the group consisting of pyridyl, pyrazinyl, pyrimidinyl, triazinyl, thiazolyl, thiophenyl, furyl, pyrazol, pyrrolyl, and imidzaolyl;

or is lower alkyl, lower alkenyl, —(CH$_2$)$_n$—Si(CH$_3$)$_3$, —(CH$_2$)$_n$—O-lower alkyl, —(CH$_2$)$_n$—S-lower alkyl, —(CH$_2$)$_q$-cycloalkyl, or —(CH$_2$)$_n$—[CH(OH)]$_m$—(CF$_2$)$_p$—CH$_q$F$_{(3-q)}$, or is —(CH$_2$)$_n$—CR$^2$—CF$_3$, wherein the two R radicals form together with the carbon atom a cycloalkyl ring;

R' is hydrogen or lower alkyl;

n is 1, 2 or 3;

m is 0 or 1;

p is 0, 1, 2, 3, 4, 5 or 6;

q is 0, 1, 2 or 3;

$R^2$ is hydrogen or lower alkyl;

$R^3$ is hydrogen, lower alkyl, —CH$_2$CF$_2$CF$_3$, CH$_2$CF$_3$, (CH$_2$)$_2$CF$_3$, CF$_3$, CHF$_2$, CH$_2$F or is aryl optionally mono, di or tri-substituted by halogen, or is —(CH$_2$)$_n$NR$^5$R$^6$ wherein $R^5$ and $R^6$ are each independently selected from hydrogen or lower alkyl;

$R^4$ is one of the following groups

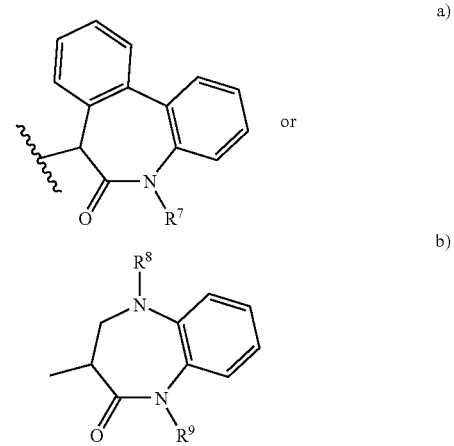

wherein $R^7$ is hydrogen, lower alkyl, —(CH$_2$)$_n$—CF$_3$ or —(CH$_2$)$_n$-cycloalkyl;

$R^8$ is hydrogen, lower alkyl, —C(O)-phenyl, —C(O)-lower alkyl, —C(O)O—(CH$_2$)$_n$-cycloalkyl, —C(O)O—(CH$_2$)$_n$-lower alkyl, —C(O)NH—(CH$_2$)$_n$-lower alkyl or —C(O)NH—(CH$_2$)$_n$-cycloalkyl;

$R^9$ is hydrogen, lower alkyl, —(CH$_2$)$_n$-cycloalkyl or —(CH$_2$)$_n$—CF$_3$;

or a pharmaceutically acceptable salt, optically pure enantiomer, racemate or diastereomeric mixture thereof and a pharmaceutically acceptable carrier.

23. A composition comprising a compound of formula

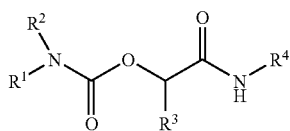

I-1 wherein
  R¹ is —(CH$_2$)$_n$-aryl or —(CH$_2$)$_n$-heteroaryl, which is unsubstituted or mono, di- or tri-substituted by lower alkyl, lower alkoxy, CF$_3$ or halogen,
  wherein heteroaryl is selected from the group consisting of pyridyl, pyrazinyl, pyrimidinyl, triazinyl, thiazolyl, thiophenyl, furyl, pyrazol, pyrrolyl, and imidzaolyl;
or is
  lower alkyl, —(CH$_2$)$_n$—O-lower alkyl, —(CH$_2$)$_n$—S-lower alkyl, —(CH$_2$)$_n$-cycloalkyl,
  —(CH$_2$)$_n$—CH$_2$F, —(CH$_2$)$_n$—CF$_3$, —(CH$_2$)$_n$—CF$_2$—CF$_3$, or —(CH$_2$)$_n$—CF$_2$—CHF$_2$,
or is
  —(CH$_2$)$_n$—CR$^2$—CF$_3$, wherein the two R radicals form together with the carbon atom a cycloalkyl ring;
  R² is hydrogen or lower alkyl;
  R³ is hydrogen, lower alkyl, —CH$_2$F, CHF$_2$, CF$_3$, aryl optionally mono, di or tri-substituted by halogen, or —(CH²)$_n$NR⁵R⁶ wherein R⁵ and R⁶ are each independently selected from hydrogen or lower alkyl;
  R⁴ is one of the following groups a)

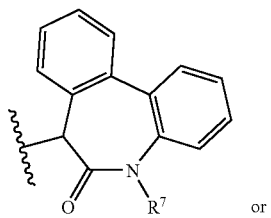

or b)

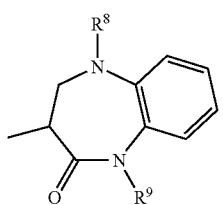

wherein
  R⁷ is lower alkyl or —(CH)$_2$-cycloalkyl;
  R⁸, R⁹ are each independently selected from hydrogen, lower alkyl, —(CH$_2$)$_n$-cycloalkyl or —C(O)-phenyl;
or a pharmaceutically acceptable salt, optically pure enantiomer, racemate or diastereomeric mixture thereof and a pharmaceutically acceptable carrier.

24. A process for preparing a compound of formula

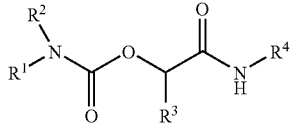

I wherein
  R¹ is —(CHR')$_q$-aryl or —(CHR')$_q$-heteroaryl, which is unsubstituted or mono, di- or tri-substituted by lower alkyl, lower alkoxy, CF$_3$ or halogen,
  wherein heteroaryl is selected from the group consisting of pyridyl, pyrazinyl, pyrimidinyl, triazinyl, thiazolyl, thiophenyl, furyl, pyrazol, pyrrolyl, and imidzaolyl;
or is
  lower alkyl, lower alkenyl, —(CH$_2$)$_n$—Si(CH$_3$)$_3$, —(CH$_2$)$_n$—O-lower alkyl, —(CH$_2$)$_n$—S-lower alkyl, —(CH$_2$)$_q$-cycloalkyl, or —(CH$_2$)$_n$—[CH(OH)]$_m$—(CF$_2$)$_p$—CH$_q$F$_{(3-q)}$,
or is
  —(CH$_2$)$_n$—CR$^2$—CF$_3$, wherein the two R radicals form together with the carbon atom a cycloalkyl ring;
  R' is hydrogen or lower alkyl;
  n is 1, 2 or 3;
  m is 0 or 1;
  p is 0, 1, 2, 3, 4, 5 or 6;
  q is 0, 1, 2 or 3;
  R² is hydrogen or lower alkyl;
  R³ is hydrogen, lower alkyl, —CH$_2$CF$_2$CF$_3$, CH$_2$CF$_3$, (CH$_2$)$_2$CF$_3$, CF$_3$, CHF$_2$, CH$_2$F or is aryl optionally mono, di or tri-substituted by halogen,
or is —(CH$_2$)$_n$NR⁵R⁶ wherein R⁵ and R⁶ are each independently selected from hydrogen or lower alkyl;
  R⁴ is one of the following groups a)

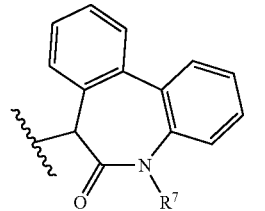

or b)

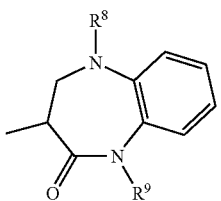

wherein
  R⁷ is hydrogen, lower alkyl, —(CH$_2$)$_n$—CF$_3$ or —(CH$_2$)$_n$-cycloalkyl;
  R⁸ is hydrogen, lower alkyl, —C(O)-phenyl, —C(O)-lower alkyl, —C(O)O—(CH$_2$)$_n$-cycloalkyl, —C(O)O—(CH$_2$)$_n$-lower alkyl, —C(O)NH—(CH$_2$)$_n$-lower alkyl or —C(O)NH—(CH$_2$)$_n$-cycloalkyl;
  R⁹ is hydrogen, lower alkyl, —(CH$_2$)$_n$-cycloalkyl or —(CH$_2$)$_n$—CF$_3$;

which comprises
reacting a compound of formula

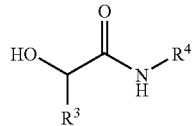
IV with a compound of formula

R¹NCO   III to produce a compound of formula

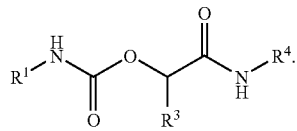
Ia

25. A process for preparing a compound of formula

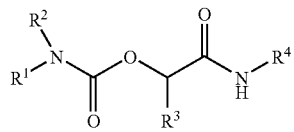
I wherein
$R^1$ is —$(CHR')_q$-aryl or —$(CHR')_q$-heteroaryl, which is unsubstituted or mono, di- or tri-substituted by lower alkyl, lower alkoxy, $CF_3$ or halogen,
wherein heteroaryl is selected from the group consisting of pyridyl, pyrazinyl, pyrimidinyl, triazinyl, thiazolyl, thiophenyl, furyl, pyrazol, pyrrolyl, and imidzaolyl;
or is
lower alkyl, lower alkenyl, —$(CH_2)_n$—$Si(CH_3)_3$, —$(CH_2)_n$—O-lower alkyl, —$(CH_2)_n$—S-lower alkyl, —$(CH_2)_q$-cycloalkyl, or —$(CH_2)_n$—$[CH(OH)]_m$—$(CF_2)_p$—$CH_qF_{(3-q)}$,
or is
—$(CH_2)_n$—$CR^2$—$CF_3$, wherein the two R radicals form together with the carbon atom a cycloalkyl ring;
R' is hydrogen or lower alkyl;
n is 1, 2 or 3;
m is 0 or 1;
p is 0, 1, 2, 3, 4, 5 or 6;
q is 0, 1, 2 or 3;
$R^2$ is hydrogen or lower alkyl;
$R^3$ is hydrogen, lower alkyl, —$CH_2CF_2CF_3$, $CH_2CF_3$, $(CH_2)_2CF_3$, $CF_3$, $CHF_2$, $CH_2F$ or is aryl optionally mono, di or tri-substituted by halogen,
or is —$(CH_2)_nNR^5R^6$ wherein $R^5$ and $R^6$ are each independently selected from hydrogen or lower alkyl;
$R^4$ is one of the following groups a)
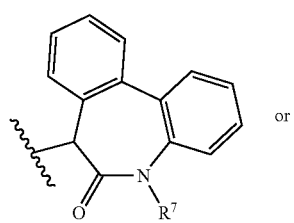
or b)
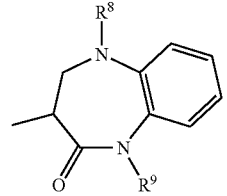

wherein
$R^7$ is hydrogen, lower alkyl, —$(CH_2)_n$—$CF_3$ or —$(CH_2)_n$-cycloalkyl;
$R^8$ is hydrogen, lower alkyl, —C(O)-phenyl, —C(O)-lower alkyl, —$C(O)O$—$(CH_2)_n$-cycloalkyl, —$C(O)O$—$(CH_2)_n$-lower alkyl, —$C(O)NH$—$(CH_2)_n$-lower alkyl or —$C(O)NH$—$(CH_2)_n$-cycloalkyl;
$R^9$ is hydrogen, lower alkyl, —$(CH_2)_n$-cycloalkyl or —$(CH_2)_n$—$CF_3$;
which comprises
reacting a compound of formula

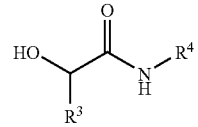
IV with a compound of formula $NHR^1R^2$   II in the presence of a suitable phosgene equivalent and a base,
to produce a compound of formula

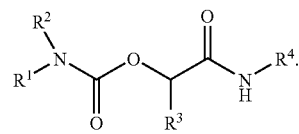
I

26. A method of treating Alzheimer's disease in a patient comprising administering to the patient a therapeutically effective amount of a compound of formula

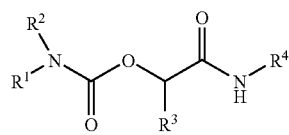
I wherein
$R^1$ is —$(CHR')_q$-aryl or —$(CHR')_q$-heteroaryl, which is unsubstituted or mono, di- or tri-substituted by lower alkyl, lower alkoxy, $CF_3$ or halogen,
wherein heteroaryl is selected from the group consisting of pyridyl, pyrazinyl, pyrimidinyl, triazinyl, thiazolyl, thiophenyl, furyl, pyrazol, pyrrolyl, and imidzaolyl;

or is lower alkyl, lower alkenyl, —(CH$_2$)$_n$—Si(CH$_3$)$_3$, —(CH$_2$)$_n$—O-lower alkyl, —(CH$_2$)$_n$—S-lower alkyl, —(CH$_2$)$_q$-cycloalkyl, or —(CH$_2$)$_n$—[CH(OH)]$_m$—(CF$_2$)$_p$—CH$_q$F$_{(3-q)}$, or is —(CH$_2$)$_n$—CR$_2$—CF$_3$, wherein the two R radicals form together with the carbon atom a cycloalkyl ring;

R' is hydrogen or lower alkyl;

n is 1, 2 or 3;

m is 0 or 1;

p is 0, 1, 2, 3, 4, 5 or 6;

q is 0, 1, 2 or 3;

R$^2$ is hydrogen or lower alkyl;

R$^3$ is hydrogen, lower alkyl, —CH$_2$CF$_2$CF$_3$, CH$_2$CF$_3$, (CH$_2$)$_2$CF$_3$, CF$_3$, CHF$_2$, CH$_2$F or is aryl optionally mono, di or tri-substituted by halogen, or is —(CH$_2$)$_n$NR$^5$R$^6$ wherein R$^5$ and R$^6$ are each independently selected from hydrogen or lower alkyl;

R$^4$ is one of the following groups

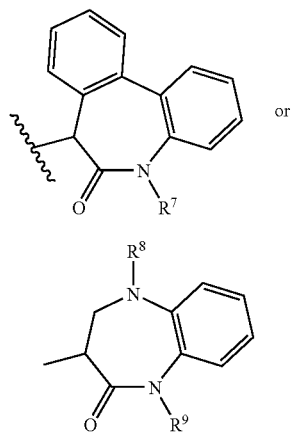

a)

b)

wherein

R$^7$ is hydrogen, lower alkyl, —(CH$_2$)$_n$—CF$_3$ or —(CH$_2$)$_n$-cycloalkyl;

R$^8$ is hydrogen, lower alkyl, —C(O)-phenyl, —C(O)-lower alkyl, —C(O)O—(CH$_2$)$_n$-cycloalkyl, —C(O)O—(CH$_2$)$_n$-lower alkyl, —C(O)NH—(CH$_2$)$_n$-lower alkyl or —C(O)NH—(CH$_2$)$_n$-cycloalkyl;

R$^9$ is hydrogen, lower alkyl, —(CH$_2$)$_n$-cycloalkyl or —(CH$_2$)$_n$—CF$_3$;

or a pharmaceutically acceptable salt, optically pure enantiomer, racemate or diastereomeric mixture thereof.

27. A method of treating Alzheimer's disease in a patient comprising administering to the patient a therapeutically effective amount of a compound of formula

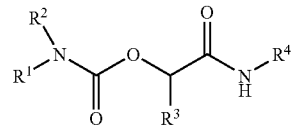

I-1 wherein

R$^1$ is —(CH$_2$)$_n$-aryl or —(CH$_2$)$_n$-heteroaryl, which is unsubstituted or mono, di- or tri-substituted by lower alkyl, lower alkoxy, CF$_3$ or halogen, wherein heteroaryl is selected from the group consisting of pyridyl, pyrazinyl, pyrimidinyl, triazinyl, thiazolyl, thiophenyl, furyl, pyrazol, pyrrolyl, and imidzaolyl;

or is lower alkyl, —(CH$_2$)$_n$—O-lower alkyl, —(CH$_2$)$_n$—S-lower alkyl, —(CH$_2$)$_n$-cycloalkyl, —(CH$_2$)$_n$—CH$_2$F, —(CH$_2$)$_n$—CF$_3$, —(CH$_2$)$_n$—CF$_2$—CF$_3$, or —(CH$_2$)$_n$—CF$_2$—CHF$_2$, or is —(CH$_2$)$_n$—CR$^2$—CF$_3$, wherein the two R radicals form together with the carbon atom a cycloalkyl ring;

R$^2$ is hydrogen or lower alkyl;

R$^3$ is hydrogen, lower alkyl, —CH$_2$F, CHF$_2$, CF$_3$, aryl optionally mono, di or tri-substituted by halogen, or —(CH$^2$)$_n$NR$^5$R$^6$ wherein R$^5$ and R$^6$ are each independently selected from hydrogen or lower alkyl;

R$^4$ is one of the following groups a)

or b)

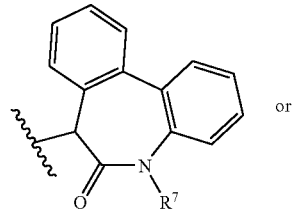

wherein

R$^7$ is lower alkyl or —(CH)$_2$-cycloalkyl;

R$^8$, R$^9$ are each independently selected from hydrogen, lower alkyl, —(CH$_2$)$_n$-cycloalkyl or —C(O)-phenyl;

or a pharmaceutically acceptable salt, optically pure enantiomer, racemate or diastereomeric mixture thereof.

* * * * *